United States Patent
Yu et al.

(10) Patent No.: US 11,186,840 B2
(45) Date of Patent: *Nov. 30, 2021

(54) CTLA-4 APTAMER CONJUGATES

(71) Applicant: CITY OF HOPE, Duarte, CA (US)

(72) Inventors: Hua Yu, Glendora, CA (US); Andreas Herrmann, Pasadena, CA (US); Marcin Tomasz Kortylewski, Monrovia, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/892,995

(22) Filed: Jun. 4, 2020

(65) Prior Publication Data

US 2020/0377890 A1 Dec. 3, 2020

Related U.S. Application Data

(63) Continuation of application No. 14/602,182, filed on Jan. 21, 2015, now Pat. No. 10,711,272.

(60) Provisional application No. 61/929,832, filed on Jan. 21, 2014.

(51) Int. Cl.
| | |
|---|---|
| *C07H 21/04* | (2006.01) |
| *C12N 15/113* | (2010.01) |
| *A61K 31/713* | (2006.01) |
| *C12N 15/115* | (2010.01) |
| *C12N 15/11* | (2006.01) |
| *A61K 45/06* | (2006.01) |
| *A61K 47/54* | (2017.01) |

(52) U.S. Cl.
CPC .......... *C12N 15/113* (2013.01); *A61K 31/713* (2013.01); *A61K 45/06* (2013.01); *A61K 47/549* (2017.08); *C12N 15/111* (2013.01); *C12N 15/115* (2013.01); *C12N 15/1138* (2013.01); *C12N 2310/11* (2013.01); *C12N 2310/12* (2013.01); *C12N 2310/13* (2013.01); *C12N 2310/14* (2013.01); *C12N 2310/16* (2013.01); *C12N 2310/3519* (2013.01); *C12N 2320/30* (2013.01); *C12N 2320/32* (2013.01)

(58) Field of Classification Search
None
See application file for complete search history.

(56) References Cited

U.S. PATENT DOCUMENTS

| | | |
|---|---|---|
| 8,829,178 B2 | 9/2014 | Barth et al. |
| 10,711,272 B2 | 7/2020 | Yu et al. |
| 2006/0246123 A1 | 11/2006 | Gilboa et al. |
| 2009/0148944 A1 | 6/2009 | Rossi et al. |
| 2010/0240732 A1 | 9/2010 | Gilboa |

OTHER PUBLICATIONS

Byrne, W.L. et al. (Nov. 15, 2011, e-published Novembers, 2011). "Targeting regulatory T cells in cancer," *Cancer Res* 71 (22):6915-6920.

Contardi, E. et al. (Nov. 20, 2005). "CTLA-4 is constitutively expressed on tumor cells and can trigger apoptosis upon ligand interaction," *Int J Cancer* 117(4):538-550.

Darlington, P.J. et al. (Jul. 15, 2005). "Hierarchical regulation of CTLA-4 dimer-based lattice formation and its biological relevance forT cell inactivation," *J Immunol* 175(2):996-1004.

Dassie, J.P. et al. (Aug. 23, 2009). "Systemic administration of optimized aptamer-siRNA chimeras promotes regression of PSMA-expressing tumors," *Nature Biotechnology* 27(9):839-849.

Herrmann, A. et al. (Oct. 1, 2010, e-published Sep. 14, 2010). "Targeting Stat3 in the myeloid compartment drastically improves the in vivo antitumor functions of adoptively transferred T cells," *Cancer Res* 70(19)7455-7464.

Kortylewski, M. et al. (Oct. 2009, e-published Sep. 13, 2009). "In vivo delivery of siRNA to immune cells by conjugation to a TLR9 agonist enhances antitumor immune responses," *Nat Biotechnol* 27(10):925-932.

Krause, D.S. et al. (Jul. 2005). "Tyrosine kinases as targets for cancer therapy," *New England Journal of Medicine* 352(2):172-187.

Kujawski, M. et al. (Dec. 1, 2010, e-published Nov. 30, 2010). "Targeting STAT3 in adoptively transferred T cells promotes their in vivo expansion and antitumor effects," *Cancer Res* 70(23):9599-9610.

Kunigal, S. et al. (May 2009). "Stat3-siRNA Induces Fas-mediated Apoptosis in vitro and in vivo in Breast Cancer," *International Journal of Oncology* 34(5):1209-1220.

McNamara, J.O. 2$^{nd}$ et al. (Aug. 2006, e-published Jun. 25, 2006). "Cell type-specific delivery of siRNAs with aptamer-siRNA chimeras," *Nat Biotechnol* 24(8):1005-1015.

Niu, J. et al. (May 2011). "Foxp3 expression in melanoma cells as a possible mechanism of resistance to immune destruction," *Cancer Immunology and Immunotherapy* 60(8):1109-1118.

Pardoll, D.M. (Mar. 22, 2012). "The blockade of immune checkpoints in cancer immunotherapy." *Nat Rev Cancer* 12(4):252-264.

(Continued)

*Primary Examiner* — Kimberly Chong
(74) *Attorney, Agent, or Firm* — Mintz, Levin, Cohn, Ferris, Glovsky and Popeo, P.C.

(57) ABSTRACT

Provided herein are, inter alia, nucleic acid compounds useful for targeting CTLA-4-expressing cells and modulating cell activity of the CTLA-4-expressing cells. The compositions provided herein may be part of pharmaceutical compositions and may be used for treatment of cancer, inflammatory diseases, infectious diseases or metabolic diseases.

14 Claims, 14 Drawing Sheets
Specification includes a Sequence Listing.

(56) References Cited

OTHER PUBLICATIONS

Santulli-Marotto, S. et al. (Nov. 1, 2003). "Multivalent RNA aptamers that inhibit CTLA-4 and enhance tumor immunity," *Cancer Res* 63(21)7483-7489.

Wheeler, L.A. et al. (Jun. 2011, e-published May 16, 2011). "Inhibition of HIV transmission in human cervicovaginal explants and humanized mice using CD4 aptamer-siRNA chimeras," *J Clin Invest* 121(6):2401-2412.

- FoxP3-GFP+
- ECM

- CD4
- Foxp3
- Hoechst

- CD8
- GrB
- Hoechst

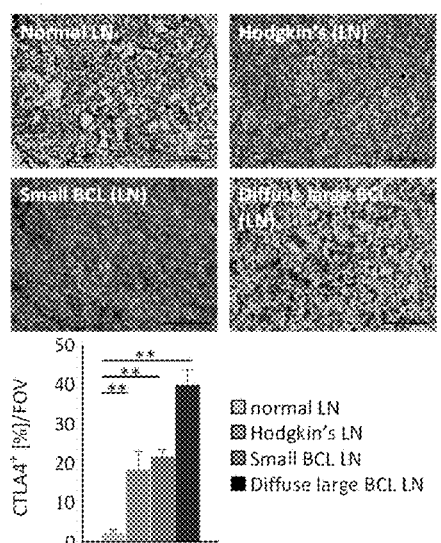
FIG.11A
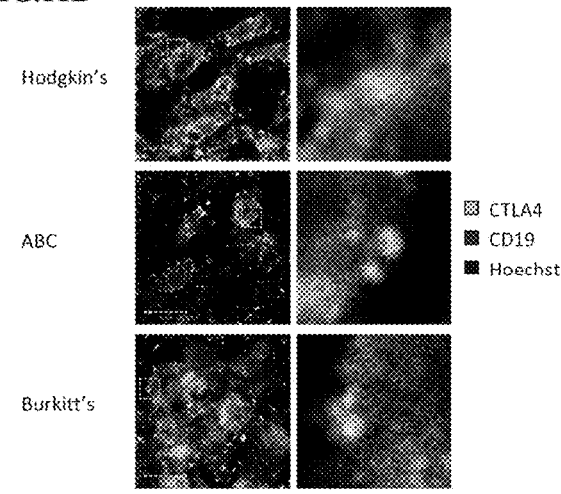
FIG.11B
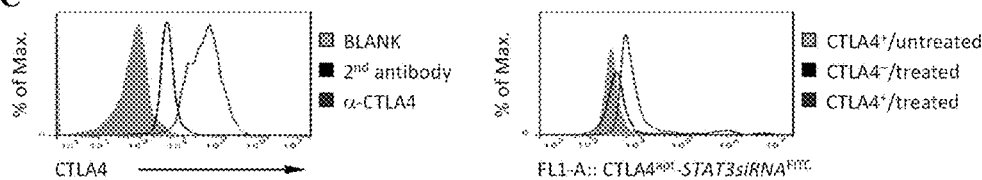
FIG.11C FIG.11D
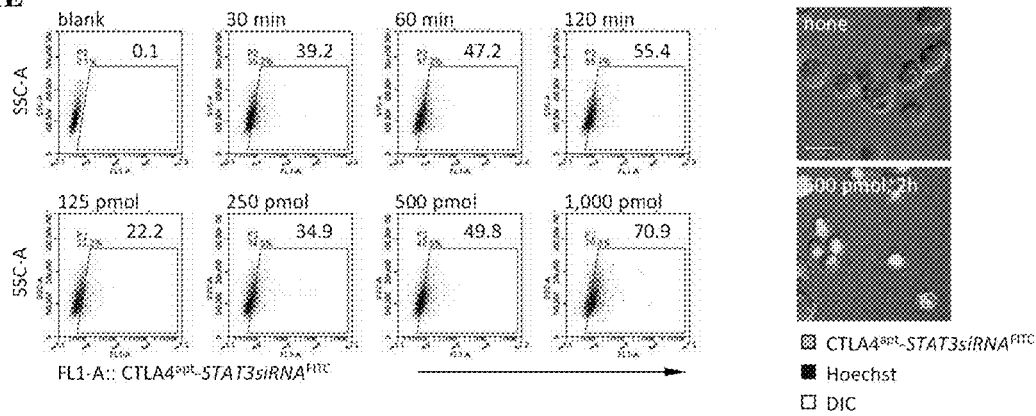
FIG.11E
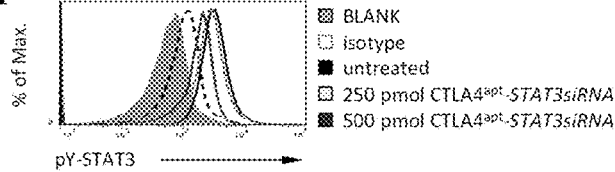 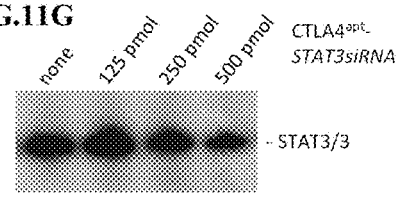
FIG.11F FIG.11G

SEQUENCE LISTING

<160> NUMBER OF SEQ ID NOS: 7

<210> SEQ ID NO 1
<211> LENGTH: 35
<212> TYPE: RNA
<213> ORGANISM: Artificial sequence
<220> FEATURE:
<223> OTHER INFORMATION: Synthetic polynucleotide

```
<400> SEQUENCE: 1
gggagagagg aagagggaug ggccgacgug ccgca                              35

<210> SEQ ID NO 2
<211> LENGTH: 37
<212> TYPE: PRT
<213> ORGANISM: Artificial sequence
<220> FEATURE:
<223> OTHER INFORMATION: Synthetic polypeptide

<400> SEQUENCE: 2

Gln Gly Leu Arg Ala Met Asp Thr Gly Leu Tyr Ile Cys Lys Val Glu
1               5                   10                  15

Leu Met Tyr Pro Pro Pro Tyr Leu Gly Ile Gly Asn Gly Thr Gln
            20                  25                  30

Ile Tyr Val Ile Asp
        35

<210> SEQ ID NO 3
<211> LENGTH: 37
<212> TYPE: PRT
<213> ORGANISM: Artificial sequence
<220> FEATURE:
<223> OTHER INFORMATION: Synthetic polypeptide

<400> SEQUENCE: 3

Gln Gly Leu Arg Ala Val Asp Thr Gly Leu Tyr Leu Cys Lys Val Glu
1               5                   10                  15

Leu Met Tyr Pro Pro Pro Tyr Tyr Val Gly Met Gly Asn Gly Thr Gln
            20                  25                  30

Ile Tyr Val Ile Asp
        35

<210> SEQ ID NO 4
<211> LENGTH: 49
<212> TYPE: RNA
<213> ORGANISM: Artificial sequence
<220> FEATURE:
<223> OTHER INFORMATION: Synthetic polynucleotide

<400> SEQUENCE: 4
gggagagagg aagagggaug ggccgacgug ccgcacgcgc uagaguacc              49

<210> SEQ ID NO 5
<211> LENGTH: 14
<212> TYPE: RNA
<213> ORGANISM: Artificial sequence
<220> FEATURE:
<223> OTHER INFORMATION: Synthetic polynucleotide

<400> SEQUENCE: 5
gguacucuag cgcg                                                    14

<210> SEQ ID NO 6
<211> LENGTH: 25
<212> TYPE: RNA
<213> ORGANISM: Artificial sequence
<220> FEATURE:
<223> OTHER INFORMATION: Synthetic polynucleotide

<400> SEQUENCE: 6 cagggguca gaucacaugg gcuaa                                         25
```

```
<210> SEQ ID NO 7
<211> LENGTH: 27
<212> TYPE: RNA
<213> ORGANISM: Artificial sequence
<220> FEATURE:
<223> OTHER INFORMATION: Synthetic polynucleotide

<400> SEQUENCE: 7
uuagcccaug ugaucugaca cccugaa                                        27
```

CTLA-4 APTAMER CONJUGATES

CROSS-REFERENCE TO RELATED APPLICATIONS

This application is a continuation of U.S. patent application Ser. No. 14/602,182, filed Jan. 21, 2015, which claims the benefit of U.S. Provisional Application No. 61/929,832, filed Jan. 21, 2014, which is hereby incorporated in its entirety and for all purposes.

STATEMENT AS TO RIGHTS TO INVENTIONS MADE UNDER FEDERALLY SPONSORED RESEARCH AND DEVELOPMENT

This invention was made with government support under grant numbers R01CA122976, R01CA146092, P50CA107399, and P30CA033572 awarded by the National Institutes of Health. The Government has certain rights in the invention.

REFERENCE TO A SEQUENCE LISTING, A TABLE OR A COMPUTER PROGRAM LISTING APPENDIX SUBMITTED AS AN ASCII TEXT FILE

The Sequence Listing written in file 048440-538C01US_SEQUENCE_LISTING_ST25.TXT, created on Jun. 3, 2020, 2,181 bytes, machine format IBM-PC, MS Windows operating system, is hereby incorporated by reference

BACKGROUND OF THE INVENTION

Recent promising human results of immunotherapies to block immune checkpoints such as cytotoxic T-lymphocyte-associated antigen 4 (CTLA4) and programmed cell death protein 1 (PD-1) (Pardoll, D. M., Nat Rev Cancer 12:252-264 (2012); Pardoll, D. M., Nat Immunol 13:1129-1132 (2012); Keir, M. E. et al., Annu Rev Immunol 26:677-704 (2008)) illustrate the importance of targeting molecules that inhibit T cell-mediated antitumor immunity. However, the immunosuppressive tumor microenvironment hampers the success of various immunotherapies. There are several intracellular checkpoints with great potential as targets to promote potent antitumor immunity. STAT3, for example, has been shown to be a crucial signaling mediator in tumor-associated immune cells, as well as in tumor cells (Yu, H. et al., Nat Rev Cancer 9:798-809 (2009); Kortylewski, M. and Yu, H., Curr Opin Immunol 20:228-233 (2008); Kortylewski, M. et al., Nat Med 11:1314-1321 (2005); Herrmann, A. et al., Cancer Res 70:7455-7464 (2010)). In tumor cells, STAT3 promotes tumor cell survival/proliferation, invasion, and immunosuppression (Yu, H., and Jove, R., Nat Rev Cancer 4:97-105 (2004)). In the tumor microenvironment, STAT3 is persistently activated in immune cells, including T cells (Kujawski, M. et al., Cancer Res 70:9599-9610 (2010); Yu, H. et al., Nat Rev Immunol 7:41-51 (2007)). CD4$^+$ T regulatory cells (T$_{Regs}$) can induce peripheral tolerance, suppressing CD8 T cell functions in various diseases including cancer (Kortylewski, M. et al., Nat Med 11:1314-1321 (2005); Curiel, T. J. et al., Nat Med 10:942-949 (2004); Shevach, E. M., Nat Rev Immunol 2:389-400 (2002); Chen, M. L. et al., Proc Natl Acad Sci USA 102: 419-424 (2005); Mempel, T. R. et al., Immunity 25:129-141 (2006); Arens, R. and Schoenberger, S. P., Immunol Rev 235:190-205 (2010)). Activated STAT3 in T cells contributes to expanding tumor-associated CD4$^+$ T$_{Regs}$ (Kortylewski, M. et al., Nat Med 11:1314-1321 (2005); Pallandre, J. R. et al., J Immunol 179:7593-7604 (2007)). Moreover, Stat3$^{-/-}$ CD8$^+$ T cells, both endogenous or adoptively transferred, mount potent antitumor immune responses compared to those with intact Stat3 (Kujawski, M. et al., Cancer Res 70:9599-9610 (2010)).

As a nuclear transcription factor lacking its own enzymatic activity, STAT3 is a challenging target for both antibody and small-molecule drugs (Yu, H., and Jove, R., Nat Rev Cancer 4:97-105 (2004); Darnell, J. E., Nat Med 11:595-596 (2005); Darnell, J. E., Jr., Nat Rev Cancer 2:740-749 (2002)). Recent pioneering work has shown the feasibility to deliver siRNA into tumor cells in vivo (McNamara, J. O., 2nd et al., Nat Biotechnol 24:1005-1015 (2006)). In particular, chimeric RNAs or DNA-RNAs consisting of a siRNA fused to nucleic acid sequences, which bind to either a cell surface ligand or an intracellular receptor with high affinity, have demonstrated therapeutic efficacy in preclinical models (McNamara, J. O., 2nd et al., Nat Biotechnol 24:1005-1015 (2006); Wheeler, L. A. et al., J Clin Invest 121:2401-2412 (2011); Kortylewski, M. et al., Nat Biotechnol 27:925-932 (2009)). The majority of such siRNA delivery technologies involves the fusion of siRNA to an aptamer, a structured RNA with high affinity to epitopes on tumor cells and virally infected epithelial cells. Applicants recently described a technology for efficient in vivo delivery of siRNA into immune cells by linking an siRNA to CpG oligonucleotide, which binds to its cognate receptor, TLR9 (Kortylewski, M. et al., Nat Biotechnol 27:925-932 (2009)). TLR9 is expressed intracellularly in cells of myeloid lineage and B cells, as well as tumor cells expressing TLR9, including human leukenuc cells (Kortylewski, M. et al., Nat Biotechnol 27:925-932 (2009); Zhang, Q. et al., Blood 121:1304-1315 (2013)). However, the CpG-siRNA approach does not directly target T cells (Kortylewski, M. et al., Nat Biotechnol 27:925-932 (2009)).

Recently, an effective way to deliver siRNA into CD4 T cells for local treatment of HIV has been developed (Wheeler, L. A. et al., J Clin Invest 121:2401-2412 (2011)). However, for cancer immunotherapy, it is also crucial to regulate CD8$^+$ effector T cells, in addition to CD4$^+$ cells. Further, it is quite plausible that selectively targeting the subpopulations of CD8$^+$ and CD4$^+$ T cells in the tumor microenvironment, rather than T cells in general, should afford more antitumor efficacy while reducing toxicity. The expression of CTLA4 is dysregulated in tumors and in tumor-associated T cells and is a promising immunotherapeutic target (Santulli-Marotto, S. et al., Cancer Res 63:7483-7489 (2003)). The broad antitumor immune response by CTLA4 blockade is thought to be mainly mediated by CD4$^+$ T cells: reducing T$_{Regs}$ and increasing helper T cells (Chen, M. L. et al., Proc Natl Acad Sci USA 102.419-424 (2005), Wing, K. et al., Science 322:271-275 (2008); Byrne, W. L. et al., Cancer Res 71:6915-6920 (2011); Peggs, K. S. et al., J Exp Med 206:1717-1725 (2009); Lenschow, D. J. et al., Annu Rev Immunol 14:233-258 (1996)). However, activated/exhausted CD8 T cells also express CTLA4 (Walunas, T. L. et al., Immunity 1:405-413 (1994); Teft, W. A. et al., Annu Rev Immunol 24:65-97 (2006); Wherry, E. J. et al., Immunity 27:670-684 (2007)).

There is a need in the art for compositions and methods of delivering modulators of cell activity (e.g., anti-tumor agents, anti-obesity agents) to cells (e.g., malignant cells, tumor-associated T cells, effector T cells) to inhibit diseases such as cancer, metastasis or metabolic diseases. The nucleic acid compounds and methods of using the same as provided herein cure these and other needs in the art.

BRIEF SUMMARY OF THE INVENTION

Provided herein are, inter alia, nucleic acid compounds useful for targeting CTLA-4-expressing cells and modulating cell activity of the CTLA-4-expressing cells. The compositions provided herein may be part of pharmaceutical compositions and may be used for treatment of a variety of different disease. For example, the compositions provided herein may be used m the treatment of cancer, inflammatory diseases, infectious diseases and metabolic diseases (e.g., diabetes).

In one aspect a nucleic acid compound including a monomeric CTLA-4 aptamer nucleic acid conjugated to a cell activity modulating nucleic acid is provided.

In another aspect, a mammalian cell including a nucleic acid compound as provided herein including embodiments thereof is provided.

In another aspect, a cellular receptor bound to a nucleic acid compound as provided herein including embodiments thereof is provided.

In another aspect, a pharmaceutical composition including a pharmaceutically acceptable excipient and a nucleic acid compound as provided herein including embodiments thereof is provided.

In another aspect, a method of treating a disease in a subject in need thereof is provided. The method includes administering to a subject a therapeutically effective amount of a nucleic acid compound as provided herein including embodiments thereof, thereby treating the subject.

In another aspect, a method of inhibiting growth of a cancer cell is provided. The method includes contacting a cancer cell with a nucleic acid compound as provided herein including embodiments thereof, thereby inhibiting growth of the cancer cell.

In another aspect, a method of inhibiting activity of a tumor-associated T cell is provided. The method includes contacting a tumor-associated T cell with a nucleic acid compound as provided herein including embodiments thereof, thereby inhibiting activity of the tumor-associated T cell.

In another aspect, a method of stimulating the immune system of a subject in need thereof is provided. The method includes administering to the subject an effective amount of a nucleic acid compound as provided herein including embodiments thereof to a subject, thereby stimulating the immune system of the subject.

In another aspect, a method of inhibiting a protein activity in a cell is provided. The method includes contacting a cell with a nucleic acid compound as provided herein including embodiments thereof, thereby forming a contacted cell. The contacted cell is allowed to express the antisense nucleic acid thereby forming a cellular antisense nucleic acid. The cellular antisense nucleic acid is allowed to inhibit a protein activity in the cell.

BRIEF DESCRIPTION OF THE DRAWINGS

(FIG. 1A) CTLA4$^{apt}$-siRNA$^{FITC}$ positive and negative CD3$^+$ T cells (CD3$^+$FITC$^+$ and CD3$^+$FITC$^-$) were isolated by FACS sorting from tumors of mice treated as indicated. Expression of Stat3 mRNA was assessed by RT-PCR. SD shown. Two-tailed student's t-test *) P <0.05, ) P<0.01, *) P<0.001. (FIG. 1B) Cellular internalization of CTLA-4$^{apt}$-Stat3siRNA into a CD8$^+$ T cell suspension was visualized by confocal microscopy. Scale bar 5 µm. (FIG. 1C) Efficient uptake of fluorescently labeled CTLA-4$^{apt}$-<Stat3siRNA by CD8$^+$ T cells. Flow cytometry analysis showing CD8$^+$ T cells positive for CTLA-4$^{apt}$-Stat3siRNA after 2 h of treatment. (FIG. 1D) Intracellular trafficking of CTLA-4$^{apt}$-Stat3siRNA through the endosomal compartment indicated by EEA-1 staining was assessed by confocal analysis of CD8 T cells treated for time points as indicated. Scale bar 5 µm. (FIG. 1E) Stat3 knock-down efficiency in vitro in CD8$^+$ T cells by CTLA-4$^{apt}$-Stat3siRNA. Stat3 expression was analyzed by RT-PCR at RNA level or (FIG. 1F) by Western blotting at the protein level from CD8$^+$ T cell lysates. (FIG. 1G) Western blot showing upregulation of CTLA-4 by CD8$^+$ T cells stimulated by IL-6. (FIG. 1H) IL-6 potently stimulates CTLA-4 accumulation in the lipid rafts of CD8 T cells. Mouse primary CD8$^+$ T cells were stimulated for with IL-6. Single cell suspensions were stained for lipid rafts and CTLA-4 and analyzed by confocal microscopy (left panel). Lipid raft domains and CTLA-4 accumulations in lipid rafts upon IL-6 treatment (white arrowheads) are shown. Scale bar 2 µm.

(FIG. 2A) In vivo uptake of locally administered CTLA-4$^{apt}$-Stat3siRNA by CD3 (upper panel) and CD8$^+$ (lower panel) T cells from lymph nodes (LN) or tumor draining lymph nodes (TDLN), respectively. Single cell suspensions were analyzed by flow cytometry. (FIG. 2B) CTLA4$^{apt}$-siRNA$^{FITC}$ positive and negative CD3$^+$ T cells (CD3$^+$FITC$^+$ and CD3$^+$ FITC$^-$) were isolated by FACS sorting from B16 melanoma tumor-bearing mice. Expression of Stat3 mRNA was assessed by RT-PCR. SD shown. Two-tailed student's t-test performed and P-value indicated. (FIG. 2C) In vivo knock-down efficiency of CTLA-4*-Stat3siRNA. Flow cytometric analysis showing pStat3 levels in CD8$^+$ T cells from tumor draining lymph nodes post CTLA-4$^{apt}$-Stat3siRNA, CTLA-4$^{apt}$-LucsiRNA, or vehicle control treatments. (FIG. 2D) Improved antigen-specific CD8$^+$ T cell effector function by CTLA-4$^{apt}$-Stat3 siRNA. CD8-OTI cells were adoptively transferred into B16-OVA tumor bearing Rag1$^{-/-}$ mice. Mice were treated four times every other day with CTLA-4$^{apt}$-Stat3siRNA, CTLA-4$^{apt}$-LucsiRNA, or left untreated after adoptive therapy. CD8$^+$ effector function was assessed by analyzing granzyme B (GrB) and interferon γ (IFNγ) in ELISPOT assay after response recall with OVA$^{SIINFEKL}$ peptide. SD shown; two-tailed student's t-test *) P<0.05, ) P<0.01, *) P<0.001. (FIG. 2E) Analysis of improved T cell function of lymphocytes isolated from tumor-draining lymph nodes after treating B16 melanoma tumor bearing mice with CTLA-4$^{apt}$-Stat3siRNA or CTLA-4$^{apt}$-LucsiRNA. ELISPOT was performed after recalling the T cell response with B16 antigen-specific peptides p15E and TRP-2, respectively. SD shown; two-tailed student's t-test *) P<0.05, ) P<0.01, *) P<0.001. (FIG. 2F) CD8$^+$ T cell exhaustion was assessed by analyzing PD-1 expression upon treating B16 tumor bearing mice with CTLA-4$^{apt}$-Stat3siRNA, CTLA-4$^{apt}$-LucsiRNA, or vehicle control (PBS) in flow cytometry.

(FIG. 3A) CTLA4$^{apt}$-Stat3siRNA via local administration reduces tumor T$_{Reg}$. FoxP3-GFP$^+$ T$_{Reg}$ cell population was imagined by in vivo multiphoton microscopy in B16 melanoma tumors upon local treatments with the indicated siRNA conjugates, or vehicle control (PBS). ECM is given by 2HG. Scale bar 200 µm. (FIG. 3B) Flow cytometry showing CD4$^+$CD25$^+$FoxP$^+$ T$_{Reg}$ cell populations in B16 melanoma tumors after treating with the indicated siRNA conjugates. (FIG. 3C) IL-10 production by GFP$^+$ T$_{Reg}$ cells isolated from tumors of FoxP3-GFP transgenic mice treated as indicated was analyzed by flow cytometry. (FIG. 3D) Lung nodule formation was determined in a lung colonization assay upon systemic administration of B16 melanoma cells. Mice were treated systemically every other day as indicated. SD shown; two-tailed student's t-test *) P<0.05, ) P<0.01, *) P<0.001. (FIG. 3E) Homing of CD4$^+$FoxP3$^+$ T$_{Reg}$ cells as well as (FIG. 3F) granzyme B$^+$ CD8$^+$ CTL infiltrating the lung was assessed in microsections of lungs after systems administration of B16 melanoma cells and systemic treatment of mice as indicated. Scale bar 100 μm. SD shown for CD8$^+$ lung infiltrating cells; two-tailed student's t-test *) P<0.05, ) P<0.01, *) P<0.001. (FIG. 3G) Growth kinetics for melanoma tumor, renal cell carcinoma (Renca), lymphoma, and colon carcinoma was assessed upon local administration of CTLA4$^{apt}$-conjugates or vehicle control. Mice were treated every other day. SD shown; two-tailed student's t-test *) P<0.05, ) P<0.01, *) P<0.001.

(FIG. 4A) CTLA4 expression by Karpas299 human T cell lymphoma was assessed by flow cytometry. (FIG. 4B) CTLA4-aptamer at 500 pmol/ml and CTLA4 protein were analyzed for colocalization in Karpas299 T cell lymphoma cells by confocal microscopy in indicated time kinetics. Scale bar 10 μm. (FIG. 4C) CTLA4 protein recognition by CTLA4-aptamer. CTLA4-aptamer$^{FITC}$ and CTLA4 protein were analyzed for interaction upon aptamer treatment for 2 h in human T cell lymphoma by co-immunoprecipitation in a dose-dependent fashion as indicated. (FIG. 4D) Flow cytometry analysis showing uptake kinetics of fluorescent CTLA-4$^{apt}$-STAT3siRNA by human Karpas299 T cell lymphoma at indicated doses and time points in vitro. (FIG. 4E) Efficacy of in vivo silencing targeting luciferase. Luciferase$^+$ Karpas299 cells engrafted subcutaneously in immune compromised mice were treated three times every other day with CTLA4$^{apt}$-LuciferasesiRNA or CTLA4-aptamer as a control. Bioluminescent non-invasive imaging was performed time points as indicated and luminescent signal was quantified (right panel). SD shown; two-tailed student's t-test *) P<0.05, ) P<0.01, *) P<0.001.

(FIG. 5A) Human T cell lymphoma tissue array was stained for CTLA4 expression and analyzed by direct immunofluorescence and (FIG. 5B) quantified. Magnified areas (dashed line) are shown in the lower left corner. Scale bar 100 μm. SD shown; two-tailed student's t-test *) P<0.05, ) P<0.01, *) P<0.001. (FIG. 5C) Tumor growth kinetics of Karpas299 T cell lymphoma engrafted into athymic nude mice treated every other day with CTLA-4$^{apt}$-STAT3siRNA, CTLA-4$^{apt}$-LucsiRNA or vehicle (PBS). (FIG. 5D) Flow cytometry showing phospho-STAT3 expression and apoptotic cell death in the human T cell lymphoma tumors treated as indicated. (FIG. 5E) Human T cell lymphoma tumor microsections prepared from mice treated as indicated were stained for Ki67$^+$ proliferative activity (left upper panels), CD31$^+$ tumor vasculature (left middle panels), and B7-H1$^+$ (left lower panels). Scale bar 100 μm. Fluorescent signals of Ki67 and B7-H1, and CD31$^+$ blood vessel length assessed by confocal microscopy were quantified (right panels) from independent FOV; bar graph shown CTLA-4$^{apt}$-STAT3siRNA (light gray), CTLA-4$^{apt}$-LucsiRNA (dark grey) or vehicle (PBS, black). SD shown; two-tailed student's t-test *) P<0.05, ) P<0.01, *) P<0.001.

(FIG. 6A) Scheme of the CTLA4$^{apt}$ with Stat3siRNA conjugate. (FIG. 6B) For in vitro uptake, total nucleated splenocytes from wild-type C57BL/6 mice were pre-stained with fluorophore-conjugated surface markers (CD4, CD8, CD19, and CD11b) and then 1×10$^6$ cells were treated with control (untreated) or FITC-conjugated CTLA4$^{apt}$-Stat3siRNA (500 pmol/ml) for 2 hrs and then analyzed immediately by flow cytometry. (FIG. 6C) For in vivo uptake, mice bearing established CT26 tumors were treated for 3 consecutive days with control (untreated), unconjugated CTLA4$^{apt}$-LucsiRNA, or FITC-conjugated CTLA4$^{apt}$-Stat3siRNA. Single-cell suspensions from tumors were analyzed for FITC-expressing cells by flow cytometry using surface markers for CD45, CD3, F4/80, CD11c, and CD19. Sequence legend: gggagagagg aagagggaug ggccgacgug ccgcacgcgc uagaguacc (SEQ ID NO:4); gguacucuag cgcg (SEQ ID NO:5); cagguguca gaucacaugg gcuaa (SEQ ID NO:6); and uuagcccaug ugaucugaca cccugaa (SEQ ID NO:7).

(FIG. 7A) Murine fibrosarcoma 8101Re and 8101Pro were analyzed for cytokine expression profiles by cytokine arrays. (FIG. 7B) Elevated IL-6 expression by fibrosarcoma 8101Pro was confirmed by RT-PCR (left) and ELISA (right). (FIG. 7C) Fibrosarcoma 8101Re and 8101Pro were engrafted in syngeneic C57BL/6 mice and tumor growth kinetics were monitored. SD shown; two-tailed student's t-test *) P<0.05, ) P<0.01, *) P<0.001. (FIG. 7D) Induction of CD8 T cell tolerance was assessed by monitoring tumor growth of fibrosarcoma 8101 Re and 8101Pro engrafted in Rag1$^{-/-}$ mice which received naïve CD8 T cells adoptively transferred when tumors reached a volume of 300 mm$^3$ (arrowhead). While 8101Re showed regression upon T cell transfer, 8101Pro growth kinetics relapsed after a short delay (day 15-23). SD shown; two-tailed student's t-test *) P<0.05, ) P<0.01, *) P<0.001. (FIG. 7E) Tumor infiltration of adoptively transferred CD8 T cells was visualized by confocal microscopy (left) and quantified (right). SD shown; two-tailed student's t-test *) P<0.05, ) P<0.01, *) P<0.001. (FIG. 7F) Tumor-induced T cell tolerance was assessed by adoptive T cell transfer to B16 melanoma bearing mice comparing antitumor activity of CD8 cells isolated from tumor bearing donor mice (triangles) to CD8 cells isolated from naïve donor mice (squares). Untreated mice were monitored as control (circles). SD shown; two-tailed student's t-test *) P<0.05, ) P<0.01, *) P<0.001.

(FIG. 8A) Scheme of CTLA4 gene full length showing exons 1-2, which represent the extracellular domain (ECD), the transmembrane spanning region coded by exon 3, and the cytoplasmic tail coded by exon 4. (FIG. 8B) The amino acid sequence of the ligand binding region (B7 binding motif) of mouse and human CTLA4 is highly conserved, (adapted from Teft, W. A. et al., Amu Rev Immunol 24:65-97 (2006)). Sequence legend: QGLRAMDTGLYICKVELMYPP-PYYLGIGNGTQIYVID (SEQ ID NO:2); QGLRAVDTG-LYLCKVELMYPPPYYVGMGNGTQIYVID (SEQ ID NO:3).

(FIG. 10A) B cell lymphoma express elevated levels of CTLA4 protein assessed from patient biopsies. (FIG. 10B) CTLA4 protein locates to the cell surface in various human B cell lymphoma as shown by colocalization studies with surface marker CD19 in various human patient biopsies. Surface area is shown magnified (right panels). (FIG. 10C) Human B cell lymphoma cell line Ly3, used as a model to study CTLA-4apt-STAT3siRNA treatment efficacy, overexpress CTLA4 protein as shown by flow cytometry. (FIG. 10D) Efficient uptake of CTLA-4apt-STAT3siRNA dependent on CTLA4 expression was analyzed by flow cytometry. (FIG. 10E) Dose- and time-dependent cellular internalization of CTLA-4apt-STAT3siRNA by Ly3 cells was determined by flow cytometry. Cellular internalization of CTLA-4apt-STAT3siRNA was acquired by confocal microscopy. Scale bar 10 µm. (FIG. 10F) STAT3 silencing efficacy mediated by CTLA-4apt-STAT3siRNA was analyzed in a dose-dependent fashion by flow cytometry as well as (FIG. 10G) demonstrated by STAT3 DNA binding activity shown by EMSA.

FIGS. 11A-11I: CTLA4 is overexpressed in human patients. FIG. 11A shows a staining against CTLA4 in a normal lymphnode and three types of B cell lymphoma (Hodgkin's, small B cell lymphoma and diffuse B cell lymphoma). CTLA4 is not present in normal lymphnodes. In Hodgkin's, small B cell lymphoma and diffuse B cell lymphoma CTLA4 is overexpressed. Therefore a CTLA4 overexpression is a common event in B cell lymphoma and CTLA4 is a target in B cell lymphoma cells. The scale bar represents 100 µm. Lower panel: The lower panel shows a numeric quantification representing the data of the upper panel in CTLA4+ area in percent. \*\*: p=0.005. FIG. 11B: CTLA4 is presented at the cell surface in human patients. FIG. 11B shows a fluorescence microscopy analysis of Hodgkin's, ABC and Burkitt B cell lymphomas. CTLA4 and CD19 (surface marker for B cells) staining. The small white dotted squares in the left panels are magnified on the right side. Therefore CTLA4 is functionally localized on the surface of B cell lymphoma cells. The scale bar represents 10 µm. FIG. 11C: CTLA4 expression in B cell lymphoma cell line Ly3. FIG. 11C shows a flow cytometry analysis of Ly3 B-cell lymphoma cells. The Ly3 cells were stained against CTLA4. As controls were used blank (solid grey) unstained cells and a 2nd antibody (black) staining. The X-axis represents the percentage of signal intensity (% of Max.) and the Y-axis represents the wavelength scale for the CTLA4 staining. FIG. 11D: CTLA4apt-STAT3siRNAFITC accumulates in B cell lymphoma cells with high CTLA4 expression. FIG. 11D shows a flow cytometry analysis of the B cell lymphoma cell line Ly3 with and without a treatment of the CTLA4apt-STAT3siRNAFITC. This cell line has two populations of CTLA4 expression (high and low). The CTLA4high population with no treatment was used as control (grey solid area). Therefore CTLA4apt-STAT3siRNAFITC only binds to cells with a high CTLA4 expression. Tins finding can be used as a tool for manipulation in B cell lymphoma cells with high CTLA4 expression. FIG. 11E: CTLA4apt-STAT3siRNAFITC uptake after 120 min. and 1,000 pmol. FIG. 11E shows a flow cytometry analysis of a kinetic uptake experiment. It has been shown, that 55% of CTLA4 positive B cell lymphoma cells are loaded after 120 minutes of incubation with 500pmol CTLA4apt-STAT3siRNAFITC. With 1,000 pmol CTLA4apt-STAT3siRNAFITC CTLA4 positive B cell lymphoma cells are loaded up to 70% with CTLA4apt-STAT3siRNAFITC. Therefore we can specifically load and manipulate CTLA4 positive B cell lymphoma cells with CTLA4apt-STAT3siRNAFITC. Right panel: CTLA4apt-STAT3siRNAFITC internalizes into B cell lymphoma cells. The right panel shows a microscopic (DIC) picture of the cells used m the left panel. FIG. 11F: STAT3 expression decreases by CTLA4apt-STAT3siRNAFITC treatment. FIG. 11F shows in a flow cytometry analysis the pSTAT3 expression after a CTLA4apt-STAT3siRNAFITC treatment in Ly3 cells. After a 72 h treatment with 500pmol CTLA4apt-STAT3siRNAFITC the pSTAT3 expression is reduced. FIG. 11G: STAT3 DNA binding decreases by CTLA4apt-STAT3siRNAFITC treatment. FIG. 11F shows an EMSA experiment and point out the decreased DNA binding of STAT3 after a CTLA4apt-STAT3siRNAFITC treatment. FIG. 11H: CTLA4apt-STAT3siRNAFITC uptake after 15 min. in multiple myeloma cells. FIG. 11H shows a flow cytometry analysis of an uptake experiment in the multiple myeloma cell line H929. It has been shown, that multiple myeloma cells show a significant uptake of CTLA4apt-STAT3siRNAFITC after 15 min. of treatment with 500pmol. Therefore multiple myeloma cells are also a target for CTLA4apt-STAT3siRNAFITC. FIG. 11I. CTLA4apt-STAT3siRNAFITC is processed by Dicer after 2 h in multiple myeloma cells. FIG. 11I shows a fluorescence microscopy analysis of the multiple myeloma cell line H929 after a CTLA4apt-STAT3siRNAFITC. The left upper panel shows cells with no treatment, the right upper panel cells after 2 h of treatment. The small white dotted square in the right upper panels is magnified in the lower panel. The circles in both lower pictures are located at the same position and show in the lower left panel CTLA4apt-STAT3siRNAFITC, in the lower right panel Dicer. Therefore CTLA4apt-STAT3siRNAFITC and Dicer are co localized. The scale bar represents 100 µm FIG. 12A: Local treatments of human B cell lymphoma tumors with CTLA4apt-STAT3siRNAFITC show a significant decrease tumor growth in vivo. FIG. 12A shows the tumor growth curve of the in vivo experiment with Ly3 (2×106 cells) engrafted human B cell lymphoma tumors. After 13 days of growth the tumors were locally treated every other day with CTLA4apt-STAT3siRNAFITC (curve with triangles) and CTLA4apt-Luciferase-siRNA (curve with squares) (782.5 pmol/dose). The vehicle is represented by the curve with diamonds. The x axis represents days the y axis the tumor volume. \*: p=0.05, \*\*: p=0.005. FIG. 12B: Systemic treatments of human B cell lymphoma tumors with CTLA4apt-STAT3siRNAFITC show a significant decreased tumor growth in vivo. FIG. 12B shows the tumor growth curve of the in vivo experiment with Ly3 (2×106 cells) engrafted human B cell lymphoma tumors. After 2 days of growth the tumors were systemically treated every other day with 782.5 pmol/dose CTLA4apt-STAT3siRNAFITC (curve with triangles) and 391.25 pmol/dose CTLA4apt-STAT3siRNAFITC (curve with squares). The vehicle is represented by the curve with diamonds. The x axis represents days the y axis the tumor volume in mm3. \*: p=0.05, \*\*: p=0.005. FIG. 12C: Local treatments of human B cell lymphoma tumors with CTLA4apt-STAT3siRNAFITC show significant effects in pSTAT3 expression, blood vessel length, amount of cl. caspase 3, BclXL expression and cell growth in vivo. FIG. 12C shows a fluorescence microscopy analysis of locally treated tumors from the experiment in FIG. 2A. The OCT slides were fixed with 2% paraformaldehyde (15 min.) followed by ice-cold methanol (10 min.). After washing with PBS and an image enhancer incubation (30 min.) the slides were blocked for 1 h at room temperature with 10% goat, 2.5% mouse and 2.5% donkey serum in PBS. Following an overnight incubation with the primary antibodies (pSTAT3, CD31, cl.caspase 3, BclXL and Ki67 all 1:50) at 4° C. in a wet chamber the slides were washed and incubated with the secondary antibody for 30 min. pSTAT3, CD31 and cl. caspase 3 is represented in red, BclXL and Ki67 is represented in green and nuclei are represented in blue. After a final washing step the slides were mounted with Mowiol® 4-88 mounting media, stored for one night at 4° C. and analyzed via fluorescence microscopy. The scale bar represents 100 µm. Right panels: The right panels shows a numeric quantification representing the data of the left panels in MFI and µm. ***: p=0.0005

DETAILED DESCRIPTION OF THE INVENTION

Definitions

Figure 1A:
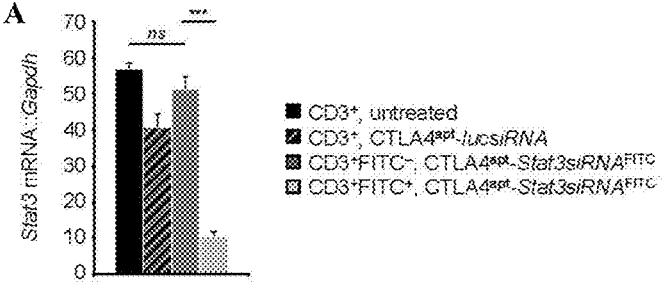
FIGS. 1A-1H: CTLA4$^{apt}$-siRNA uptake and gene silencing in T cells including CD8$^+$ T cells.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable non-cyclic straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term heteroalkyl should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic non-aromatic versions of "alkyl"

and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A cycloalkylene and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently (e.g., biphenyl). A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, —NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —$NO_2$, in a number ranging from zero to (2m'+1), where m is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —CO$_2$R, —CONR'R", —OC(O)NR'R", —NR"C(O)R', —NR'—C(O)NR"R"', —NR"C(O)$_2$R', —NR—C(NR'R"R"')═NR"", —NR—C(NR'R")═NR"', —S(O)R', —S(O)$_2$R', —S(O)$_2$NR'R", —NRSO$_2$R', —NR'NR'R", —ONR'R", —NR'C═(O)NR"NR"'R"", —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R"', and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$-U-, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R"')$_d$—, where s and d are independently integers of from 0 to 3, and X' is —O—, —NR'—, —S—, —S(O)—, —S(O)$_2$—, or —S(O)$_2$NR'—. The substituents R, R', R", and R"' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_2$Cl, SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O) NHNH$_2$, —NHC═(O) NH$_2$, —NHSO$_2$H, —NHC═(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section below.

"Nucleic acid" refers to deoxyribonucleotides or ribonucleotides and polymers thereof in either single- or double-stranded form, or complements thereof. The term polynucleotide refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules m physiological environments or as probes on a biochip. Mixtures of naturally occurring nucleic adds and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

Nucleic acid is "operably linked" when it is placed into a functional relationship with another nucleic acid sequence. For example, DNA for a presequence or secretory leader is operably linked to DNA for a polypeptide if it is expressed as a preprotein that participates m the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "probe" or "primer", as used herein, is defined to be one or more nucleic add fragments whose specific hybridization to a sample can be detected. A probe or primer can be of any length depending on the particular technique it will be used for. For example, PCR primers are generally between 10 and 40 nucleotides in length, while nucleic add probes for, e.g., a Southern blot, can be more than a hundred nucleotides in length. The probe may be unlabeled or labeled as described below so that its binding to the target or sample can be detected. The probe can be produced from a source of nucleic acids from one or more particular (preselected) portions of a chromosome, e.g., one or more clones, an isolated whole chromosome or chromosome fragment, or a collection of polymerase chain reaction (PCR) amplification products. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) Science 767-773; Johnston (1998) Curr. Biol. 8: R171-R174; Schummer (1997) Biotechniques 23: 1087-1092; Kern (1997) Biotechniques 23: 120-124; U.S. Pat. No. 5,143,854).

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe. Alternatively, a method using high affinity interactions may achieve the same results where one of a pair of binding partners binds to the other, e.g., biotin, streptavidin.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al, 1989 *Molecular Cloning: A Laboratory Manual*, 18.1-18.88.

An "inhibitory nucleic acid" is a nucleic acid (e.g. DNA, RNA, polymer of nucleotide analogs) that is capable of inhibiting the function of a target protein (e.g., STAT3) by binding to a target nucleic acid (e.g. an mRNA translatable into STAT3) and reducing transcription of the target nucleic acid (e.g. mRNA from DNA) or reducing the translation of the target nuclei add (e.g. mRNA) or altering transcript splicing. In embodiments, the inhibitory nucleic acid is a nucleic acid that is capable of binding (e.g. hybridizing) to a target nucleic acid (e.g. an mRNA translatable into an STAT3) and reducing translation of the target nucleic acid. The target nucleic acid is or includes one or more target nucleic acid sequences to which the inhibitory nucleic acid binds (e.g. hybridizes). In embodiments, an inhibitory nucleic acid is or includes a sequence (also referred to herein as an "antisense nucleic acid sequence") that is capable of hybridizing to at least a portion of a target nucleic acid at a target nucleic acid sequence. An example of an inhibitory nucleic acid is an antisense nucleic acid. Thus, in embodiments, the inhibitory nucleic acid is an antisense nucleic acid.

In embodiments, the inhibitory nucleic acid is a ribozyme. A "ribozyme" as provided herein refers to a ribonucleic acid capable of enzymatically modifying RNA (e.g., cleaving, splicing).

In embodiments, the inhibitory nucleic acid is an RNA decoy. An "RNA decoy" as provided herein is an RNA molecule, which inhibits the function of a protein (e.g., viral protein or cellular protein) by binding the protein. The RNA decoy may inhibit protein function by preventing the interaction between a target protein (e.g., HIV Tat) and its natural interaction partners (e.g., TAR). Further, the binding of an RNA decoy to a target protein may alter the subcellular location of the target protein thereby inhibiting its activity.

An "antisense nucleic acid" as referred to herein is a DNA or RNA molecule that is complementary to at least a portion of a specific target nucleic acid (e.g. an mRNA translatable into a protein) and is acapable of reducing transcription of the target nucleic acid (e.g. mRNA from DNA) or reducing the translation of the target nucleic acid (e.g. mRNA) or altering transcript splicing (e.g. single stranded morpholino oligo). See, e.g., Weintraub, *Scientific American*, 262:40 (1990). Typically, synthetic antisense oligonucleotides are generally between 15 and 25 bases in length. Thus, antisense nucleic acids are capable of hybridizing to (e.g. selectively hybridizing to) a target nucleic acid (e.g. target mRNA). In embodiments, the antisense nucleic acid hybridizes to the target nucleic acid sequence (e.g. mRNA) under stringent hybridization conditions. In embodiments, the antisense nucleic acid hybridizes to the target nucleic acid (e.g. mRNA) under moderately stringent hybridization conditions. Antisense nucleic acids may comprise naturally occurring nucleotides or modified nucleotides such as, e.g., phosphorothioate, methylphosphonate, and -anomeric sugar-phosphate, backbonemodified nucleotides.

In the cell, the antisense nucleic acids hybridize to the corresponding mRNA, forming a double-stranded molecule. The antisense nucleic acids interfere with the translation of the mRNA, since the cell will not translate an mRNA that is double-stranded. The use of antisense methods to inhibit the in vitro translation of genes is well known in the art (Marcus-Sakura, *Anal. Biochem.*, 172:289, (1988)). Further, antisense molecules which bind directly to the DNA may be used. Antisense nucleic acids may be single or double stranded nucleic acids. Non-limiting examples of antisense nucleic acids include siRNAs (including their derivatives or pre-cursors, such as nucleotide analogs), short hairpin RNAs (shRNA), micro RNAs (miRNA) and small nucleolar RNAs (snoRNA) or certain of their derivatives or pre-cursors.

A "siRNA," "small interfering RNA," "small RNA," or "RNAi" as provided herein refers to a nucleic acid that forms a double stranded RNA, which double stranded RNA has the ability to reduce or inhibit expression of a gene or target gene (e.g. when expressed in the same cell as the gene or target gene). The complementary portions of the nucleic acid that hybridize to form the double stranded molecule typically have substantial or complete identity. In one embodiment, a siRNA or RNAi is a nucleic acid that has substantial or complete identity to a target gene and forms a double stranded siRNA. In embodiments, the siRNA inhibits gene expression by interacting with a complementary cellular mRNA thereby interfering with the expression of the complementary mRNA. Typically, the nucleic acid is at least about 15-50 nucleotides in length (e.g., each complementary sequence of the double stranded stRNA is 15-50 nucleotides in length, and the double stranded siRNA is about 15-50 base pairs m length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length.

The term "recombinant" when used with reference, e.g., to a cell, or nucleic add, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. Transgenic cells and plants are those that express a heterologous gene or coding sequence, typically as a result of recombinant methods.

The term "exogenous" refers to a molecule or substance (e.g., a compound, nucleic acid or protein) that originates from outside a given cell or organism. For example, an "exogenous promoter" as referred to herein is a promoter that does not originate from the plant it is expressed by. Conversely, the term "endogenous" or "endogenous promoter" refers to a molecule or substance that is native to, or originates within, a given cell or organism.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "aptamer" as provided herein refers to short oligonucleotides (e.g. deoxyribonucleotides), which fold into molecular structures that bind with high affinity and specificity to proteins, peptides, and small molecules. Aptamers can be selected in vitro from very large libraries of randomized sequences by the process of systemic evolution of ligands by exponential enrichment (SELEX as described in Ellington A D, Szostak J W (1990) In vitro selection of RNA molecules that bind specific ligands. Nature 346:818-822; Tuerk C, Gold L (1990) Systematic evolution of ligands by exponential enrichment: RNA ligands to bacteriophage T4 DNA polymerase. Science 249:505-510) or by developing SOMAmers (slow off-rate modified aptamers) (Gold L et al. (2010) Aptamer-based multiplexed proteomic technology for biomarker discovery. PLoS ONE 5(12):e15004). Applying the SELEX and the SOMAmer technology includes for instance adding functional groups that mimic amino add side chains to expand the aptamer's chemical diversity. As a result high affinity aptamers for almost any protein target are enriched and identified. Aptamers exhibit many desirable properties for targeted drug delivery, such as ease of selection and synthesis, high binding affinity and specificity, low immunogenicity, and versatile synthetic accessibility. To date, a variety of anti-cancer agents (e.g. chemotherapy drugs, toxins, and siRNAs) have been successfully delivered to cancer cells in vitro using aptamers.

As used herein, the term "conjugated" when referring to two moieties means the two moieties (e.g., a monomeric CLTA-4 aptamer nucleic acid and a cell activity modulating nucleic acid) are bonded, wherein the bond or bonds connecting the two moieties may be covalent or non-covalent. In embodiments, the two moieties are covalently bonded to each other (e.g. directly or through a covalently bonded intermediary). In embodiments, the two moieties are non-covalently bonded (e.g. through ionic bond(s), van der Waal's bond(s)/interactions, hydrogen bond(s), polar bond(s), or combinations or mixtures thereof).

As used herein, the term "about" means a range of values including the specified value, which a person of ordinary skill in the art would consider reasonably similar to the speeded value. In embodiments, the term "about" means within a standard deviation using measurements generally acceptable in the art. In embodiments, about means a range extending to +/−10% of the specified value. In embodiments, about means the specified value.

The terms "protein", "peptide", and "polypeptide" are used interchangeably to denote an amino acid polymer or a set of two or more interacting or bound amino add polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino adds, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same baste chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino add, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are silent variations," which are one species of conservatively modified variations. Every nucleic add sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

The terms "identical" or percent "identity," in the context of two or more nucleic adds or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

The phrase "selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

For specific proteins described herein (e.g., STAT3, FoxP3, CTLA-4), the named protein includes any of the protein's naturally occurring forms, or variants that maintain the protein transcription factor activity (e.g., within at least 50%, 80%, 90%, 95%, 96%, 97%, 98%, 99% or 100% activity compared to the native protein). In some embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference or functional fragment thereof.

The term "CTLA-4" as provided herein includes any of the Cytotoxic T-Lymphocyte Antigen 4 (CTLA-4) protein naturally occurring forms, homologs or variants that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the CTLA-4 protein is the protein as identified by the NCBI sequence reference GI:21361212. In embodiments, the CTLA-4 protein is the protein as identified by the NCBI sequence reference GI:21361212 or functional fragment thereof. In embodiments, the CTLA-4 protein includes the sequence of SEQ ID NO:2 or SEQ ID NO:3. In embodiments, the CTLA-4 protein is encoded by a nucleic acid sequences corresponding to Gene ID: 1493.

A "STAT3 gene" as referred to herein includes any of the recombinant or naturally-occurring forms of the gene encoding Signal transducer and Activator of transcription 3 (STAT3), homologs or variants thereof that maintain STAT3 protein activity (e.g. within at least 50%, 80%, 90%, 95%, 96%, 97%, 98%, 99% or 100% activity compared to STAT3). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring STAT3 polypeptide. In embodiments, the STAT3 gene is substantially identical to the nucleic acid identified by the NCBI reference number Gene ID: 6774 or a variant having substantial identity thereto.

A "FoxP3 gene" as referred to herein includes any of the recombinant or naturally-occurring forms of the gene encoding Forkhead Box P3 (FoxP3), homologs or variants thereof that maintain FoxP3 protein activity (e.g. within at least 50%, 80%, 90%, 95%, 96%, 97%, 98%, 99% or 100% activity compared to FoxP3). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring FoxP3 polypeptide. In embodiments, the FoxP3 gene is substantially identical to the nucleic acid identified by the NCBI reference number Gene ID:50943 or a variant having substantial identity thereto.

"Anti-cancer agent" is used in accordance with its plain ordinary meaning and refers to a composition (e.g. compound, drug, antagonist, inhibitor, modulator) having anti-neoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxalaplatin, carboplatin), anthracenedione (e.g., mitoxantrone), substituted urea (e.g., hydroxyurea), methyl hydrazine derivative (e.g., procarbazine), or adrenocortical suppressant (e.g., mitotane, aminoglutethimide), epipodophyllotoxins (e.g., etoposide).

Further examples of anti-cancer agents include, but are not limited to, antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosts gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone, mismatched double stranded RNA; monoclonal antibody; mycobacterial cell wall extract; nitric oxide modulators; oxaliplatin; panomifene; pentrozole; phosphatase inhibitors, plasminogen activator inhibitor; platinum complex; platinum compounds; prednisone; proteasome inhibitors, protein A-based immune modulator; protein kinase C inhibitor; protein kinase C inhibitors, protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibody (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, C1-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the nucleic acid compound described herein can be co-administered with conventional immunotherapeutic agents including, but not limited to, immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y, or $^{131}$I, etc.).

In a further embodiment, the nucleic acid compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

The term "sample" includes sections of tissues such as biopsy and autopsy samples, and frozen sections taken for histological purposes. Such samples include blood and blood fractions or products (e.g., bone marrow, serum, plasma, platelets, red blood cells, and the like), sputum, tissue, cultured cells (e.g., primary cultures, explants, and transformed cells), stool, urine, other biological fluids (e.g., prostatic fluid, gastric fluid, intestinal fluid, renal fluid, lung fluid, cerebrospinal fluid, and the like), etc. A sample is typically obtained from a "subject" such as a eukaryotic organism, most preferably a mammal such as a primate, e.g., chimpanzee or human; cow; dog; cat; a rodent, e.g., guinea pig, rat, mouse; rabbit; or a bird; reptile; or fish. In some embodiments, the sample is obtained from a human.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Disease" or "condition" refer to a state of being or health status of a patient or subject capable of being treated with a compound, pharmaceutical composition, or method provided herein. In embodiments, the disease is cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma), an infectious disease (e.g., HIV infection), an inflammatory disease (e.g., rheumatoid arthritis) or a metabolic disease (e.g., diabetes). In embodiments, the disease is a disease related to (e.g. caused by) an increase in the level of a STAT transcription factor (e.g. STAT1, STAT2, STAT3, STAT4, STAT5A, STAT5B, or STAT6), STAT phosphorylation, or a STAT transcription factor or STAT pathway activity, or pathway activated by a STAT transcription. In some embodiments, the disease is cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma). In embodiments, the disease is a viral disease (e.g. HIV infection associated disease). In embodiments, the viral disease is associated with STAT3-dependent immunosuppression.

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinifomi carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

As used herein, an "inflammatory disease" refers to a disease or disorder associated with abnormal or altered inflammation. Inflammation is a biological response initiated by the immune system as part of the healing process in response to a pathogen, damaged cells or tissues or irritants. Chronic inflammation can lead to a variety of diseases. Inflammatory diseases include, but are not limited to, atherosclerosis, allergies, asthma, rheumatoid arthritis, transplant rejection, celiac disease, chronic prostatitis, inflammatory bowel diseases, pelvic inflammatory diseases, and inflammatory myopathies.

As used herein, "metabolic disorders" refer to diseases or disorders involving abnormal metabolism of a variety of molecules and substances including, for example, glucose, carbohydrates, amino acids, and organic acids. Metabolic disorders include, but are not limited to, disorders of glucose metabolism (e.g., type I and type II diabetes), disorders of carbohydrate metabolism, e.g., glycogen storage disease, disorders of amino acid metabolism, e.g., phenylketonuria, maple syrup urine disease, glutaric acidemia type 1, urea cycle disorder or urea cycle defects, e.g., carbamoyl phosphate synthetase I deficiency, disorders of organic acid metabolism (organic acidurias), e.g., alcaptonuria, disorders of fatty acid oxidation and mitochondrial metabolism, e.g., medium-chain acyl-coenzyme A dehydrogenase deficiency, disorders of porphyrin metabolism, e.g., acute intermittent porphyria, disorders of purine or pyrimidine metabolism, e.g., Lesch-Nyhan syndrome, disorders of steroid metabolism, e.g., lipoid congenital adrenal hyperplasia, congenital adrenal hyperplasia, disorders of mitochondrial function, e.g., Kearns-Sayre syndrome, disorders of peroxisomal function, e.g., Zellweger syndrome, and lysosomal storage disorders, e.g., Gaucher's disease, and Niemann Pick disease.

As used herein, the term "infectious disease" refers to diseases or disorders associate with infection, presence and/or growth of a pathogenic agent in a host subject. Infectious pathogenic agents include, but are not limited to, viruses, bacteria, fungi, protozoa, multicellular parasites and aberrant proteins, e.g., prions. Viruses associated with infectious disease include but are not limited to, herpes simplex viruses, cytomegalovirus, Epstein-Barr virus, Varicella-zoster virus, herpes viruses, Vesicular stomatitis virus, Hepatitis viruses, Rhinovirus, Coronavirus, Influenza viruses, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Simian Immunodeficiency viruses (SIV), Human Immunodeficiency viruses (HIV). Bacteria associated with infectious disease include, but are not limited to, *M. tuberculosis*, *Salmonella* species, *E. coli*, *Chlamydia* species, *Staphylococcus* species, *Bacillus* species, and *Pseudomonas* species.

The term "associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma) or viral disease (e.g., HIV infection associated disease)) is caused by (in whole or in part), or a symptom of the disease is caused by (in whole or in part) the substance or substance activity or function. For example, a symptom of a disease or condition associated with an increase in STAT3 activity may be a symptom that results (entirely or partially) from an increase in STAT3 activity (e.g., increase in STAT3 transcriptional activation, increase in STAT3 activation of a signal transduction or signaling pathway). As used herein, what is described as being associated with a disease, if a causative agent, could be a target for treatment of the disease. For example, a disease associated with increased STAT3 activity (e.g., increase in STAT3 transcriptional activation, increase in STAT3 activation of a signal transduction or signaling pathway), may be treated with an agent (e.g., compound as described herein) effective for decreasing the level of activity of STAT3 or STAT3 pathway. For example, a disease associated with STAT3, may be treated with an agent (e.g., compound as described herein) effective for decreasing the level of activity of STAT3 or a downstream component or effector of STAT3. For example, a symptom of a disease or condition associated with an increase in STAT (e.g., STAT1, STAT2, STAT3, STAT4, STAT5A, STAT5B, or STAT6) activity may be a symptom that results (entirely or partially) from an increase in STAT (e.g., STAT1, STAT2, STAT3, STAT4, STAT5A, STAT5B, or STAT6) activity (e.g., increase in STAT (e.g., STAT1, STAT2, STAT3, STAT4, STAT5A, STAT5B, or STAT6) transcriptional activation, increase in STAT (e.g., STAT1, STAT2, STAT3, STAT4, STAT5A, STAT5B, or STAT6) activation of a signal transduction or signaling pathway).

As used herein, what is described as being associated with a disease, if a causative agent, could be a target for treatment of the disease. For example, a disease associated with increased STAT (e.g. STAT1, STAT2, STAT3, STAT4, STAT5A, STAT5B, or STAT6) activity (e.g., increase in STAT (e.g., STAT1, STAT2, STAT3, STAT4, STAT5A, STAT5B, or STAT6) transcriptional activation, increase in STAT (e.g., STAT1, STAT2, STAT3, STAT4, STAT5A, STAT5B, or STAT6) activation of a signal transduction or signaling pathway), may be treated with an agent (e.g., compound as described herein) effective for decreasing the level of activity of a STAT transcription factor (e.g. STAT1, STAT2, STAT3, STAT4, STAT5A, STAT5B, or STAT6) or a STAT transcription factor (e.g., STAT1, STAT2, STAT3, STAT4, STAT5A, STAT5B, or STAT6) pathway. For example, a disease associated with a STAT transcription factor (e.g., STAT1, STAT2, STAT3, STAT4, STAT5A, STAT5B, or STAT6) may be treated with an agent (e.g., compound as described herein) effective for decreasing the level of activity of a STAT transcription factor (e.g. STAT1, STAT2, STAT3, STAT4, STAT5A, STAT5B, or STAT6) or a downstream component or effector of a STAT transcription factor (e.g., STAT1, STAT2, STAT3, STAT4, STAT5A, STAT5B, or STAT6).

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance. For example, certain methods herein treat cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma). For example certain methods herein treat cancer by decreasing or reducing or preventing the occurrence, growth, metastasis, or progression of cancer; or treat cancer by decreasing a symptom of cancer. Symptoms of cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma) would be known or may be determined by a person of ordinary skill in the art.

The term "treating" and conjugations thereof, include prevention of an injury, pathology, condition, or disease (e.g. preventing the development of one or more symptoms of cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)). For example certain methods herein treat viral disease (e.g., HIV infection associated disease) by decreasing or reducing or preventing the occurrence, growth, or progression of the virus infection or virus; or treat viral disease (e.g., HIV infection associated disease) by decreasing a symptom of viral disease (e.g., HIV infection associated disease).

Where combination treatments are contemplated, it is not intended that the agents (i.e. nucleic acid compounds) described herein be limited by the particular nature of the combination. For example, the agents described herein may be administered in combination as simple mixtures as well as chemical hybrids. An example of the latter is where the agent is covalently linked to a targeting carrier or to an active pharmaceutical. Covalent binding can be accomplished in many ways, such as, though not limited to, the use of a commercially available cross-linking agent.

An "effective amount" is an amount sufficient to accomplish a stated purpose (e.g. achieve the effect for which it is administered, treat a disease, reduce enzyme activity, reduce one or more symptoms of a disease or condition, reduce viral replication in a cell). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein (e.g. STAT3) relative to the absence of the antagonist. A "function disrupting amount," as used herein, refers to the amount of antagonist required to disrupt the function of an enzyme or protein relative to the absence of the antagonist. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington; The Science and Practice of Pharmacy*, 20th Edition, 2003, Gennaro, Ed., Lippincott, Williams & Wilkins).

"Patient" or "subject in need thereof" refers to a living organism suffering from or prone to a disease or condition that can be treated by using the methods provided herein. The term does not necessarily indicate that the subject has been diagnosed with a particular disease, but typically refers to an individual under medical supervision. Non-limiting examples include humans, other mammals, bovines, rats, mice, dogs, monkeys, goat, sheep, cows, deer, and other non-mammalian animals. In embodiments, a patient is human.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. Contacting may include allowing two species to react, interact, or physically touch, wherein the two species may be a nucleic acid compound as described herein and a cell (e.g., cancer cell).

"Modulate" or "modulating" refers to the suppression, enhancement or induction of a function or condition. For example, the nucleic acid compounds provided herein including embodiments thereof can modulate cancer by inhibition or activation of cellular gene activity (e.g., inhibition of STAT3 activity). For example, nucleic acid compounds including a STAT3 siRNA can inhibit STAT3 activity in T cell lymphoma cells thereby inhibiting or reducing growth of the T cell lymphoma cells.

As defined herein, the term "inhibition", "inhibit", "inhibiting" and the like in reference to an siRNA or protein-inhibitor interaction means negatively affecting (e.g., decreasing) the activity or function of the protein (e.g. decreasing gene transcription or translation) relative to the activity or function of the protein in the absence of the inhibitor. In embodiments, inhibition refers to reduction of a disease or symptoms of disease (e.g., cancer). In embodiments, inhibition refers to a reduction in the activity of a signal transduction pathway or signaling pathway (e.g. cell cycle). Thus, inhibition includes, at least in part, partially or totally blocking stimulation, decreasing, preventing, or delaying activation, or inactivating, desensitizing, or down-regulating transcription, translation, signal transduction or enzymatic activity or the amount of a protein (e.g. a cellular protein or a viral protein). In embodiments, inhibition refers to inhibition of STAT3. In embodiments, inhibition refers to inhibition of FoxP3.

The terms "inhibitor," "repressor" or "antagonist" or "downregulator" interchangeably refer to a substance that results in a detectably lower expression or activity level as compared to a control. The inhibited expression or activity can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control. An "inhibitor" is a siRNA, (e.g., shRNA, miRNA, snoRNA), compound or small molecule that inhibits cellular function (e.g., replication) e.g., by binding, partially or totally blocking stimulation, decrease, prevent, or delay activation, or inactivate, desensitize, or down-regulate signal transduction, gene expression or enzymatic activity necessary for protein activity. Inhibition as provided herein may also include decreasing or blocking a protein activity (e.g., activation of STAT3) by expressing a mutant form of said protein thereby decreasing or blocking its activity.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The term "aberrant" as used herein refers to different from normal. When used to described enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

Nucleic Acid Compositions

The nucleic acid compounds provided herein including embodiments thereof are capable of modulating (i.e. activating, inhibiting) cellular activities by modulating the activity of cellular proteins and/or nucleic acids. Non-limiting examples of cellular proteins modulated by the nucleic acid compounds provided herein include transcription factors (e.g., STAT proteins, SMAD proteins, forkhead proteins, steroid hormone receptors, growth hormone receptors, progesterone receptors, estrogen receptors, androgen receptors, E26 transformation-specific (ETS) transcription factor); cytokines (e.g., interleukin-6, interleukin-6-like cytokines, pro-inflammatory cytokines); cellular receptors (e.g., receptor tyrosine kinases (e.g., ErbB protein family or epidermal growth factor receptor (EGFR)); non-receptor tyrosine kinases (e.g., cytokine receptors); oncogenes (e.g., Src, Janus kinases (JAKS), Abl kinases, Bruton's tyrosine kinase (BTK), protein kinase B kinases (PKB/Akt kinase), protein kinase C (PKC)); and signaling molecules (e.g., phosphatases (e.g., SHP1, SHP2, T cell protein tyrosine phosphatase (TcPTP)), kinases (e.g., tyrosine kinases)).

The nucleic acid compounds provided herein include a monomeric CTLA-4 aptamer nucleic acid conjugated to a cell activity modulating nucleic acid. Thus, in one aspect a nucleic acid compound including a monomeric CTLA-4 aptamer nucleic acid conjugated to a cell activity modulating nucleic acid is provided. A monomeric CTLA-4 aptamer nucleic acid as provided herein is a nucleic acid capable of binding a Cytotoxic T-Lymphocyte Antigen 4 (CTLA-4) receptor or functional fragment thereof. In embodiments, the monomeric CTLA-4 aptamer nucleic acid includes a single stranded nucleic acid or a double stranded nucleic acid. In embodiments, the monomeric CTLA-4 aptamer nucleic acid includes a single stranded nucleic acid and a double stranded nucleic acid. In embodiments, the monomeric CTLA-4 aptamer nucleic acid is a single stranded nucleic acid. In embodiments, the monomeric CTLA-4 aptamer nucleic acid is a double stranded nucleic acid. In embodiments, the monomeric CTLA-4 aptamer nucleic acid includes an RNA. In embodiments, the monomeric CTLA-4 aptamer nucleic acid includes a DNA. In embodiments, the monomeric CTLA-4 aptamer nucleic acid is an RNA. In embodiments, the monomeric CTLA-4 aptamer nucleic acid is a DNA. In embodiments, the monomeric CTLA-4 aptamer nucleic acid is capable of binding a CTLA-4 receptor. In embodiments, the monomeric CTLA-4 aptamer nucleic acid binds a CTLA-4 receptor without activating the CTLA-4 receptor. In embodiments, the monomeric CTLA-4 aptamer nucleic acid specifically binds a CTLA-4 receptor. In embodiments, the monomeric CTLA-4 aptamer nucleic acid specifically binds a sub-cellular compartment (e.g. endosome) associated CTLA-4. In embodiments, the monomeric CTLA-4 aptamer nucleic acid includes the sequence of SEQ ID NO: 1. In embodiments, the monomeric CTLA-4 aptamer nucleic acid is the sequence of SEQ ID NO:1.

A monomeric CTLA-4 aptamer nucleic acid as provided herein is a nucleic acid that includes a single copy of a given aptamer unit (a monomeric aptamer unit) capable of binding CTLA-4. The monomeric CTLA-4 aptamer nucleic acid provided herein including embodiments thereof is not multimeric. Thus, the monomeric CTLA-4 aptamer nucleic acid provided herein including embodiments thereof does not include a plurality of the same aptamer unit. In embodiments, the monomeric CTLA-4 aptamer nucleic acid does not include a plurality of the same or a different aptamer unit. In embodiments, the monomeric CTLA-4 aptamer nucleic acid includes no more than one aptamer unit.

The nucleic acid compounds provided herein include a cell activity modulating (e.g., inhibiting, activating) nucleic acid. A "cell activity modulating nucleic acid" is a nucleic acid (e.g. DNA, RNA, polymer of nucleotide analogs) that is capable of binding to a cellular target (e.g., nucleic acid or protein) and modulating its activity and/or function. A cell activity modulating nucleic acid may be a nucleic acid modulating transcription of a target nucleic acid (e.g., mRNA from DNA) or modulating the translation of the target nucleic acid (e.g., mRNA) or altering transcript splicing. In embodiments, the cell activity modulating nucleic acid is a nucleic acid that is capable of binding (e.g. hybridizing) to a target nucleic acid (e.g. an mRNA translatable into an STAT3) and modulating translation of the target nucleic acid. The target nucleic acid is or includes one or more target nucleic acid sequences to which the cell activity modulating nucleic acid binds (e.g. hybridizes). In embodiments, a cell activity modulating nucleic acid is or includes an antisense nucleic acid sequence that is capable of hybridizing to at least a portion of a target nucleic acid at a target nucleic acid sequence. Thus, in embodiments, the cell activity modulating nucleic acid is an antisense nucleic acid. In embodiments, the cell activity modulating nucleic acid is a single stranded nucleic acid. In embodiments, the cell activity modulating nucleic acid is a double stranded nucleic acid.

In embodiments, the cell activity modulating nucleic acid is an inhibitory nucleic acid. In embodiments, the inhibitory nucleic acid is an antisense nucleic acid, an RNA decoy or a ribozyme. In embodiments, the antisense nucleic acid is a siRNA. In embodiments, the cell activity modulating nucleic acid is an antisense nucleic acid, an RNA decoy, a ribozyme, a small hairpin RNA, a micro RNA or an siRNA. In embodiments, the siRNA is an anti-cancer siRNA. In embodiments, the siRNA is an anti-viral siRNA. In embodiments, the siRNA is an anti-inflammatory siRNA. In embodiments, the siRNA is an anti-obesity siRNA. In embodiments, the siRNA is a human siRNA. In embodiments, the siRNA is a mouse siRNA. In embodiments, the siRNA is a reporter gene siRNA. In embodiments, the reporter gene siRNA is a luciferase siRNA. In embodiments, the siRNA is a FoxP3 siRNA. In embodiments, the siRNA is an anti-tyrosine kinase siRNA. In embodiments, the siRNA is a Signal Transducer and Activator of Transcription (STAT) siRNA. In embodiments, the STAT siRNA is a STAT3 siRNA. A STAT3 siRNA as provided herein is an antisense nucleic acid that is at least partially complementary to at least a portion of a target nucleic acid sequence, such as an mRNA molecule, that encodes at least a portion of the STAT3 protein.

A cell activity modulating nucleic acid as provided herein is capable of modulating the function and/or activity of a cellular target protein (e.g., FoxP3, STAT3). Cellular target proteins as provided herein include viral or bacterial proteins expressed by a cell (e.g., upon infection). Thus, a cell activity modulating (e.g., inhibiting, activating) nucleic acid as provided herein may modulate viral and cellular proteins in a cell.

In embodiments, the cell activity modulating nucleic acid modulates a transcription factor. In embodiments, the transcription factor is a STAT protein. In embodiments, the transcription factor is a SMAD protein. In embodiments, the transcription factor is a forkhead protein. In embodiments, the transcription factor is a steroid hormone receptor. In embodiments, the transcription factor is a growth hormone receptor. In embodiments, the transcription factor is a progesterone receptor. In embodiments, the transcription factor is an estrogen receptor. In embodiments, the transcription factor is an androgen receptor. In embodiments, the transcription factor is an E26 transformation-specific (ETS) transcription factor.

In embodiments, the cell activity modulating nucleic acid modulates a cytokine. In embodiments, the cytokine is interleukin-6. In embodiments, the cytokine is an interleukin-6-like cytokine. In embodiments, the cytokine is a pro-inflammatory cytokine.

In embodiments, the cell activity modulating nucleic acid modulates a cellular receptor. In embodiments, the cellular receptor is a receptor tyrosine kinase. In embodiments, the receptor tyrosine kinase is an ErbB protein family receptor kinase. In embodiments, the receptor tyrosine kinase is an epidermal growth factor receptor kinase. In embodiments, the cellular receptor is a non-receptor tyrosine kinase. In embodiments, the non-receptor tyrosine kinase is a cytokine receptor.

In embodiments, the cell activity modulating nucleic acid modulates an oncogene. In embodiments, the oncogene is a Src kinase. In embodiments, the oncogene is a Janus kinase. In embodiments, the oncogene is an Abl kinase. In embodiments, the oncogene is a BTK kinase. In embodiments, the oncogene is a PKB/Akt kinase. In embodiments, the oncogene is a PKC kinase.

In embodiments, the cell activity modulating nucleic acid modulates a signaling molecule. In embodiments, the signaling molecule is a phosphatase. In embodiments, the phosphatase is a SHP1 or a SHP2 phosphatase. In embodiments, the phosphatase is a T cell protein tyrosine phosphatase. In embodiments, the signaling molecule is a kinase. In embodiments, the kinase is a tyrosine kinase.

In embodiments, the monomeric CTLA-4 aptamer nucleic acid is conjugated to the cell activity modulating nucleic acid through a linker. A linker as provided herein is or includes a bond, a nucleic acid sequence, multiple nucleic acid sequences, a DNA sequence, multiple DNA sequences, an RNA sequence, multiple RNA sequences, a nucleic acid analog sequence, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, the linker includes a linker nucleic acid sequence. In embodiments, the linker nucleic acid sequence is a double-stranded linker nucleic acid sequence. In embodiments, the linker nucleic acid sequence is a single-stranded linker nucleic acid sequence. In embodiments, the monomeric CTLA-4 aptamer nucleic acid is connected to the cell activity modulating nucleic acid through a linker nucleic acid sequence. Where the monomeric CTLA-4 aptamer nucleic acid is connected to the cell activity modulating nucleic acid through a linker nucleic acid sequence, the linker nucleic acid sequence may be a single-stranded linker nucleic acid sequence or a double-stranded linker nucleic acid sequence.

In embodiments, the monomeric CTLA-4 aptamer nucleic acid is connected to the cell activity modulating nucleic acid through a hybridized nucleic acid overhang. Where the monomeric CTLA-4 aptamer nucleic acid is connected to the cell activity modulating nucleic acid through a hybridized nucleic acid overhang, the monomeric CTLA-4 aptamer nucleic acid includes a first single nucleic acid strand and the cell activity modulating nucleic acid includes a second single nucleic acid strand, wherein the first nucleic acid strand includes a nucleic acid sequence that is complementary to a nucleic acid sequence included in the second single nucleic acid strand (both single nucleic acid strands including their respective complementary sequences being collectively a "hybridized nucleic acid overhang"). In embodiments, the hybridized nucleic acid overhang is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs long. In embodiments, the complementary nucleic acid sequence in the hybridized nucleic acid overhang is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs long. In embodiments, the first and second single nucleic acid strands in the hybridized nucleic acid overhang are complementary throughout their entire lengths.

In embodiments, the linker nucleic acid sequence is connected to the monomeric CTLA-4 aptamer nucleic acid through a hybridized nucleic acid overhang. Where the linker nucleic acid sequence is connected to the monomeric CTLA-4 aptamer nucleic acid through a hybridized nucleic acid overhang, the linker nucleic acid includes a first single nucleic acid strand and the monomeric CTLA-4 aptamer nucleic acid includes a second single nucleic acid strand, wherein the first nucleic acid strand includes a nucleic acid sequence that is complementary to a nucleic acid sequence included in the second single nucleic acid strand (both single nucleic acid strands including their respective complementary sequences being collectively a "hybridized nucleic acid overhang"). In embodiments, the hybridized nucleic acid overhang is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs long. In embodiments, the complementary nucleic acid sequence in the hybridized nucleic acid overhang is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs long. In embodiments, the first and second single nucleic acid strands in the hybridized nucleic acid overhang are complementary throughout their entire lengths.

In embodiments, the linker nucleic acid sequence is connected to the cell activity modulating nucleic acid through a hybridized nucleic acid overhang. Where the linker nucleic acid sequence is connected to the cell activity modulating nucleic acid through a hybridized nucleic acid overhang, the linker nucleic acid includes a first single nucleic acid strand and the cell activity modulating nucleic acid includes a second single nucleic acid strand, wherein the first nucleic acid strand includes a nucleic acid sequence that is complementary to a nucleic acid sequence included in the second single nucleic acid strand (both single nucleic acid strands including their respective complementary sequences being collectively a "hybridized nucleic acid overhang"). In embodiments, the hybridized nucleic acid overhang is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs long. In embodiments, the complementary nucleic acid sequence in the hybridized nucleic acid overhang is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 base pairs long. In embodiments, the first and second single nucleic acid strands in the hybridized nucleic acid overhang are complementary throughout their entire lengths.

In embodiments, the linker includes a non-nucleic acid spacer. In embodiments, the monomeric CTLA-4 aptamer nucleic acid is connected to the cell activity modulating nucleic acid through a non-nucleic acid spacer. In embodiments, the non-nucleic acid spacer is a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, the non-nucleic acid spacer is a substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, the non-nucleic acid spacer is an unsubstituted $C_1$-$C_{20}$ alkylene, unsubstituted 2 to 20 membered heteroalkylene, unsubstituted $C_3$-$C_8$ cycloalkylene, unsubstituted 3 to 8 membered heterocycloalkylene, unsubstituted $C_6$-$C_{10}$ arylene, or unsubstituted 5 to 10 membered heteroarylene. In embodiments, the non-nucleic acid spacer is an unsubstituted $C_1$-$C_{20}$ alkylene (e.g. a $C_5$-$C_{20}$ alkylene, $C_8$-$C_{20}$ alkylene, $C_{10}$-$C_{20}$ alkylene, $C_{15}$-$C_{20}$ alkylene, $C_{18}$-$C_{20}$ alkylene or $C_{20}$ alkylene).

In embodiments, the linker includes a linker nucleic acid sequence and a non-nucleic acid spacer. Where the linker includes a linker nucleic acid sequence and a non-nucleic acid spacer, the monomeric CTLA-4 aptamer nucleic acid may be connected to a non-nucleic acid spacer through a hybridized nucleic acid overhang and the non-nucleic acid spacer may be connected to the cell activity modulating nucleic acid. In embodiments, the monomeric CTLA-4 aptamer nucleic acid is connected to a hybridized nucleic acid overhang through a non-nucleic acid spacer and the hybridized nucleic acid overhang is connected to the cell activity modulating nucleic acid. In embodiments, the non-nucleic acid spacer connects the cell activity modulating nucleic acid to the 3' terminal end of the linker nucleic acid sequence. In embodiments, the linker connects the cell activity modulating nucleic acid to the 3' terminal end of the monomeric CTLA-4 aptamer nucleic acid.

Sequences:

SEQ ID NO: 1
5' GGG AGA GAG GAA GAG GGA UGG GCC GAC GUG CCG CA 3'

SEQ ID NO: 2 (B7 binding motif of human CTLA-4):
5' QGLRAMDTGLYICKVELMYPPPYYLGIGNGTQIYVID 3'

SEQ ID NO: 3: (B7 binding motif of murine CTLA-4)
5' QGLRAVDTGLYLCKVELMYPPPYYVGMGNGTQIYVID 3'

Cellular Compositions

In another aspect, a mammalian cell including a nucleic acid compound as provided herein including embodiments thereof is provided. In embodiments, the cell expresses CTLA-4. In embodiments, the cell is a malignant cell. In embodiments, the cell is a lymphoma cell or a myeloma cell. In embodiments, the cell is a lymphoma cell. In embodiments, the cell is a myeloma cell. In embodiments, the lymphoma cell is a B cell lymphoma cell or a T cell lymphoma cell. In embodiments, the lymphoma cell is a B cell lymphoma cell. In embodiments, the lymphoma cell is a T cell lymphoma cell. In embodiments, the cell is an infected cell. In embodiments, the cell is an HIV-infected cell.

In embodiments, the cell is a non-malignant cell. In embodiments, the cell is an immune cell. In embodiments, the cell is a T cell. In embodiments, the T cell is a CD4-positive T cell, a CD8-positive T cell or a regulatory T cell. A "regulatory T cell" or "suppressor T cell" as provided herein is a T cell which modulates the immune system, maintains tolerance to self-antigens, and abrogates autoimmune diseases. Regulatory T cells are capable of shutting down immune responses after invading organisms such as viruses or bacteria have been successfully eliminated. Regulatory T cells further preventing autoimmunity by elimination auto-reactive immune cells. Non-limiting examples of surface molecules expressed by regulatory T cells are CD4, CD25, CTLA-4 and Foxp3.

In embodiments, the regulatory T cell is a tumor-associated regulatory T cell. A "tumor-associated regulatory T cell" as provided herein is a regulatory T cell in a tumor environment, which after having encountered a tumor-associated (sell) or tumor-specific (neo) antigen in the tumor environment has become activated. Under the influence of the immunosuppressive tumor microenvironment the tumor-associated regulatory T cell suppresses a tumor-eliminating immune response and enables tumor growth and expansion by promoting angiogenesis or metastasis, regulating inflammation, and suppressing antitumor adaptive immune responses. In embodiments, the tumor-associated regulatory T cell expresses Foxp3. In embodiments, the tumor-associated regulatory T cell expresses CTLA-4.

In embodiments, the cell is a B cell. In embodiments, the cell is a myeloid cell. In embodiments, the cell includes a vesicle including the nucleic acid compound.

In another aspect, a cellular receptor bound to a nucleic acid compound as provided herein including embodiments thereof is provided. In embodiments, the cellular receptor forms part of a cell. In embodiments, the cellular receptor forms part of a vesicle within the cell. In embodiments, the cell is a malignant cell. In embodiments, the cell is a lymphoma cell or a myeloma cell. In embodiments, the cell is a lymphoma cell. In embodiments, the cell is a myeloma cell. In embodiments, the lymphoma cell is a B cell lymphoma cell or a T cell lymphoma cell. In embodiments, the lymphoma cell is a B cell lymphoma cell. In embodiments, the lymphoma cell is a T cell lymphoma cell. In embodiments, the cell is an infected cell. In embodiments, the cell is an HIV-infected cell.

In embodiments, the cell is a non-malignant cell. In embodiments, the cell is an immune cell. In embodiments, the cell is a T cell. In embodiments, the T cell is a CD4-positive T cell, a CD8-positive T cell or a regulatory T cell. In embodiments, the regulatory T cell is a tumor-associated regulatory T cell. In embodiments, the tumor-associated regulatory T cell expresses Foxp3. In embodiments, the tumor-associated regulatory T cell expresses CTLA-4. In embodiments, the cell is a B cell. In embodiments, the cell is a myeloid cell.

Pharmaceutical Compositions

In another aspect, a pharmaceutical composition including a pharmaceutically acceptable excipient and a nucleic acid compound as provided herein including embodiments thereof (e.g., an aspect, embodiment, table, figure, claim, sequence listing or example) is provided. In embodiments, the nucleic acid compound as provided herein including embodiments thereof is included in a therapeutically effective amount. In embodiments, the pharmaceutical composition includes a second therapeutic agent. In embodiments, the second therapeutic agent is an anti-cancer agent. In embodiments, the second agent is an anti-viral agent. In embodiments, the pharmaceutical composition includes a second agent (e.g. therapeutic agent) in a therapeutically effective amount.

Methods of Treatment

In another aspect, a method of treating a disease in a subject in need thereof is provided. The method includes administering to a subject a therapeutically effective amount of a nucleic acid compound as provided herein including embodiments thereof, thereby treating the subject.

The methods provided herein including embodiments thereof may be used to treat cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma). For example the methods provided herein including embodiments thereof treat cancer by decreasing or reducing or preventing the occurrence, growth, metastasis, or progression of cancer; or treat cancer by decreasing a symptom of cancer. Symptoms of cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma) would be known or may be determined by a person of ordinary skill in the art. In embodiments, the disease is cancer. In embodiments, the cancer is metastatic cancer, renal cancer, colon cancer, lung cancer, melanoma, lymphoma or leukemia. In embodiments, the cancer is melanoma. In embodiments, the cancer is lymphoma.

In embodiments, the disease is an infectious disease. In embodiments, the infectious disease is caused by HIV. In embodiments, the disease is a parasitic disease.

The methods provided herein including embodiments thereof treat inflammatory diseases (e.g. autoimmune diseases, rheumatoid arthritis, asthma, celiac diseases) by decreasing or reducing or preventing the occurrence, growth, or progression of the inflammatory diseases (e.g. autoimmune diseases, rheumatoid arthritis, asthma, celiac diseases); or treat inflammatory diseases (e.g. autoimmune diseases, rheumatoid arthritis, asthma, celiac diseases) by decreasing a symptom of inflammatory diseases (e.g. autoimmune diseases, rheumatoid arthritis, asthma, celiac diseases). In embodiments, the disease is an inflammatory disease.

The methods provided herein including embodiments thereof treat metabolic diseases. Thus, in embodiments, the disease is a metabolic disease. In embodiments, the disease is diabetes.

In another aspect, a method of inhibiting growth of a cancer cell is provided. The method includes contacting a cancer cell with a nucleic acid compound as provided herein including embodiments thereof, thereby inhibiting growth of the cancer cell. In embodiments, the cancer cell includes a level of CTLA-4 greater than a non-cancer cell. In embodiments, the level of CTLA-4 (e.g., level of CTLA-4 protein) is about 2×, 3×, 4×, 5×, 6×, 7×, 8×, 9×, 10×, 20×, 30×, 40×, 50×, 60×, 70×, 80×, 90× or 100× greater than a non-cancer cell. In embodiments, the level of CTLA-4 (e.g., level of CTLA-4 protein) is at least about 2×, 3×, 4×, 5×, 6×, 7×, 8×, 9×, 10×, 20×, 30×, 40×, 50×, 60×, 70×, 80×, 90× or 100× greater than a non-cancer cell.

In embodiments, the cancer cell includes a level of STAT3 greater than a non-cancer cell. In embodiments, the level of STAT3 (e.g., level of STAT3 protein) is about 2×, 3×, 4×, 5×, 6×, 7×, 8×, 9×, 10×, 20×, 30×, 40×, 50×, 60×, 70×, 80×, 90× or 100× greater than a non-cancer cell. In embodiments, the level of STA3 (e.g., level of STAT3 protein) is at least about 2×, 3×, 4×, 5×, 6×, 7×, 8×, 9×, 10×, 20×, 30×, 40×, 50×, 60×, 70×, 80×, 90× or 100× greater than a non-cancer cell.

In embodiments, the method includes inducing apoptosis of the cancer cell. In embodiments, the method includes inducing apoptosis in a cancer cell but not in a non-cancer cell. In embodiments, the method includes inducing apoptosis in a cancer cell in a patient but not in a non-cancer cell in the same patient. In embodiments, the method includes inducing apoptosis in a cancer cell but not in a non-cancer cell of the same cell type as the cancer cell (e.g. T cell, B cell, skin cell, kidney cell, lung cell, breast cell, pancreatic cell, colorectal cell, prostate cell). In embodiments, the cancer cell is in an organ. In embodiments, the cancer cell is in a lymph node. In embodiments, the cancer cell is in bone marrow.

In another aspect, a method of inhibiting activity of a tumor-associated T cell is provided. The method includes contacting a tumor-associated T cell with a nucleic acid compound as provided herein including embodiments thereof, thereby inhibiting activity of the tumor-associated T cell. In embodiments, the tumor-associated T cell includes a level of CTLA-4 greater than a non-tumor-associated T cell. In embodiments, the level of CTLA-4 (e.g., level of CTLA-4 protein) is about 2×, 3×, 4×, 5×, 6×, 7×, 8×, 9×, 10×, 20×, 30×, 40×, 50×, 60×, 70×, 80×, 90× or 100× greater than a non-cancer cell. In embodiments, the level of CTLA-4 (e.g., level of CTLA-4 protein) is at least about 2×, 3×, 4×, 5×, 6×, 7×, 8×, 9×, 10×, 20×, 30×, 40×, 50×, 60×, 70×, 80×, 90× or 100× greater than a non-cancer cell. In embodiments, the tumor-associated T cell includes a level of STAT3 greater than a non-tumor-associated T cell. In embodiments, the level of STAT3 (e.g., level of STAT3 protein) is about 2×, 3×, 4×, 5×, 6×, 7×, 8×, 9×, 10×, 20×, 30×, 40×, 50×, 60×, 70×, 80×, 90× or 100× greater than a non-cancer cell. In embodiments, the level of STA3 (e.g., level of STAT3 protein) is at least about 2×, 3×, 4×, 5×, 6×, 7×, 8×, 9×, 10×, 20×, 30×, 40×, 50×, 60×, 70×, 80×, 90× or 100× greater than a non-cancer cell. In embodiments, the tumor-associated T cell expresses CD4. In embodiments, the tumor-associated T cell expresses CD25. In embodiments, the tumor-associated T cell expresses FoxP3.

In another aspect, a method of stimulating the immune system of a subject in need thereof is provided. The method includes administering to the subject an effective amount of a nucleic acid compound as provided herein including embodiments thereof to a subject, thereby stimulating the immune system of the subject. The stimulating may include maturation, differentiation, or proliferation of natural killer cells, T cells, monocytes, or macrophages. In embodiments, the stimulating includes an increase in a $T_H1$-type immune response. In embodiments, the stimulating includes increases in $T_H1$-type immune responses. In embodiments, the method includes stimulating a plasmacytoid dendritic cell, myeloid dendritic cell, myeloid-derived suppressor cell, macrophage, B cell, activated NK cell, or activated neutrophil. In embodiments, the stimulating includes increasing the activity of a cytotoxic T cell. In embodiments, the cytotoxic T cell is a tumor-specific cytotoxic T cell.

In another aspect, a method of inhibiting a protein activity in a cell is provided. The method includes contacting a cell with a nucleic acid compound as provided herein including embodiments thereof, thereby forming a contacted cell. The contacted cell is allowed to express the antisense nucleic acid thereby forming a cellular antisense nucleic acid. The cellular antisense nucleic acid is allowed to inhibit a protein activity in the cell. In embodiments, the protein is a STAT protein (e.g. STAT1, STAT2, STAT3, STAT4, STAT5A, STAT5B, or STAT6). In embodiments, the STAT protein is a STAT-3 protein. In embodiments, the cell is a cancer cell. In embodiments, the cell is a tumor-associated T cell.

In another aspect, a method of modulating a protein activity in a cell is provided. The method includes contacting a cell with a nucleic acid compound as provided herein including embodiments thereof, thereby forming a contacted cell. The contacted cell is allowed to express the cell activity modulating nucleic acid thereby forming a cellular cell activity modulating nucleic acid. The cellular cell activity modulating nucleic acid is allowed to modulate a protein activity in the cell. In embodiments, the cellular cell activity modulating nucleic acid activates a protein activity in the cell.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

EXAMPLES

Intracellular therapeutic targets defining tumor immunosuppression in both tumor cells and T cells remain intractable. Here, Applicants show that covalently linking siRNA to an aptamer (apt), a RNA molecule that selectively binds to CTLA4, allows gene silencing in exhausted CD8 T cells and T regulatory cells in tumor, as well as CTLA4-expressing malignant T cells. CTLA4 expression is upregulated in $CD8^+$ T cells in the tumor milieu. $CTLA4^{apt}$-STAT3siRNA treatments result in the chimera internalization into tumor-associated $CD8^+$ T cells, silencing of STAT3 and activation of tumor antigen-specific T cells. Both local and systemic administrations of $CTLA4^{apt}$-STAT3siRNA significantly reduce tumor-associated regulatory T cells. Applicants further show that $CTLA4^{apt}$-STAT3siRNA potently inhibits tumor growth and metastasis in various mouse tumor models. Importantly, many human blood malignant T cells express CTLA4, and $CTLA4^{apt}$-STAT3siRNA treatments of immunodeficient mice bearing human T cell lymphoma cause tumor cell apoptosis and tumor growth inhibition. Using $CTLA4^{apt}$ as an siRNA delivery strategy, Applicants have successfully demonstrated silencing of human and mouse STAT3 genes, as well as the luciferase gene in T cells in vivo. Collectively, Applicants have developed a novel approach that allows gene silencing in both tumor-associated T cells and tumor cells to inhibit tumor growth and metastasis.

$CTLA4^{apt}$-siRNA Uptake and Gene Silencing in T Cells

Figure 1B:
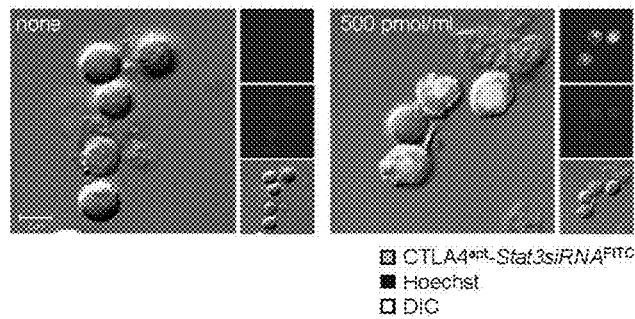
Figure 1C:
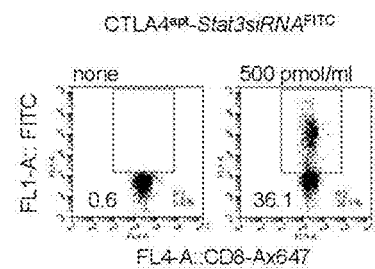
Figure 1D:
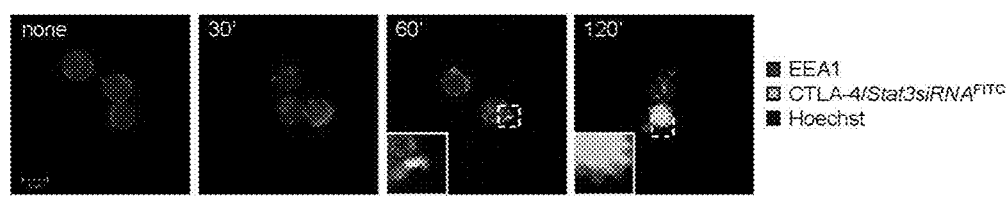
Figure 1E:
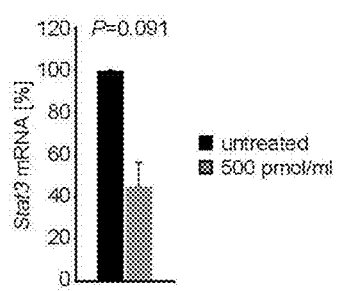
Figure 1F:
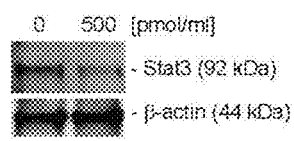
Figure 6A:
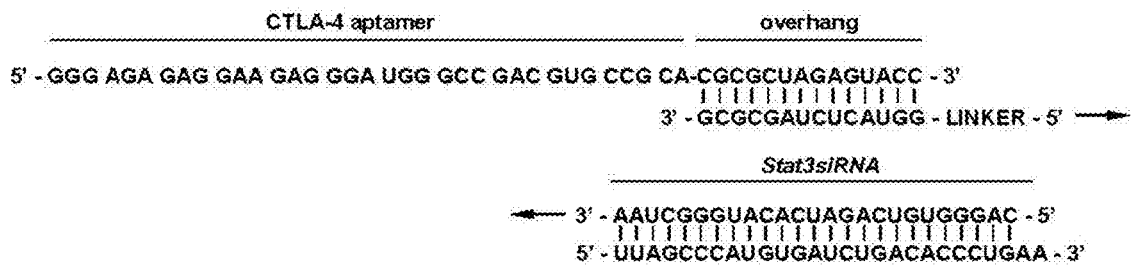
FIGS. 6A-6C: CTLA4$^{apt}$ design and uptake in vitro and in vivo.
Figure 6B:
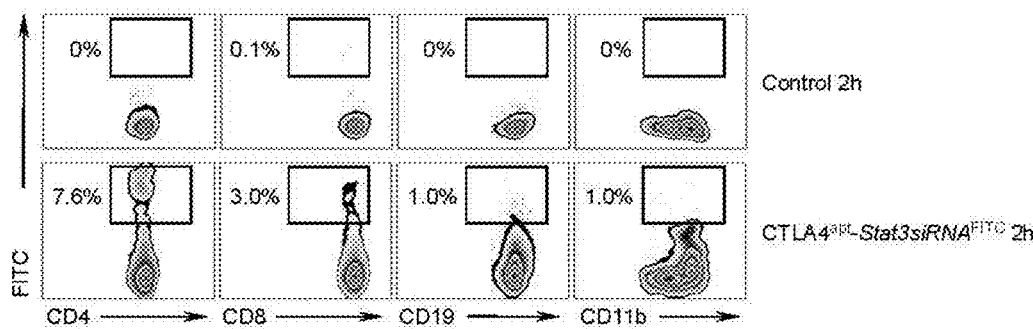
Figure 6C:
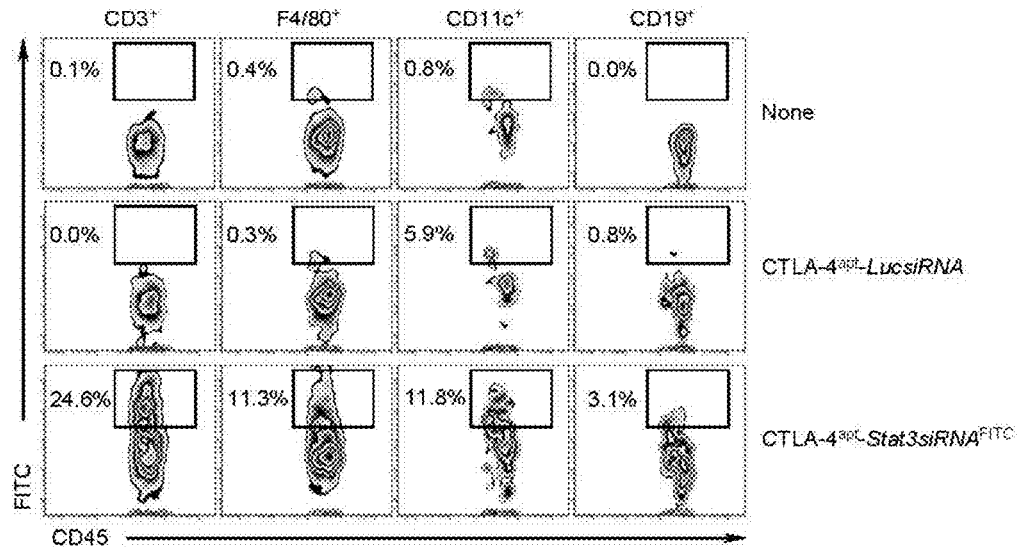

Applicants synthesized the CTLA4 targeting aptamer based on published sequences (Santulli-Marotto, S. et al., *Cancer Res* 63:7483-7489 (2003)), and chemically modified it to protect its biostability (Connolly, B. A. et al., *Biochemistry* 23:3443-3453 (1984); Spitzer, S. and Eckstein, F., *Nucleic Acids Res* 16:11691-11704 (1988); Rettig, G. R. and Behlke, M. A., *Mol Ther* 20:483-512 (2011)), followed by linking it to a mouse Stat3siRNA (FIG. 6A). Applicants tested primary mouse splenic cells to assess specific uptake of the CTLA4aptamer-Stat3siRNA ($CTLA4^{apt}$-Stat3siRNA) in immune cell populations in vitro. Even though $CD4^+$ and $CD8^+$ T cells preferentially internalized $CTLA4^{apt}$-Stat3siRNA (FIG. 6B), immune cells such as macrophages and dendritic cells also took up the chimera in vivo, but to a less extent (FIG. 6C). Applicants then treated a progressive variant of fibrosarcoma tumors (Dubey, P. et al., *J Exp Med* 185:695-705 (1997)) with $CTLA4^{apt}$-Stat3siRNA, to assess the silencing efficiency of $CTLA4^{apt}$-Stat3siRNA in various immune subsets within the tumor. $CD3^+$ T cells including both $CD8^+$ and $CD4^+$ T cells that internalized the $CTLA4^{apt}$-Stat3siRNA (FITC labeled) showed significant Stat3 gene silencing in vivo (FIG. 1A). Applicants isolated $CD8^+$ T cells to confirm that $CTLA4^{apt}$-siRNA underwent cellular internalization and exerted a gene silencing effect. Flow cytometry and live cell confocal microscopy indicated that $CD8^+$ T cells internalized CTLA4$^{apt}$-siRNA in vitro (FIG. 1B, C), trafficking through the endosomal compartment (FIG. 1D). Real time RT-PCR and Western blotting further validated target gene silencing in these cells (FIG. 1E, F).

Figure 1G:
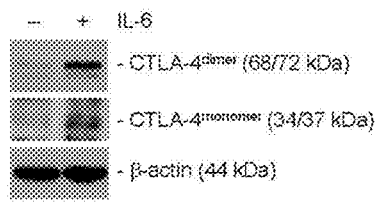
Figure 1H:
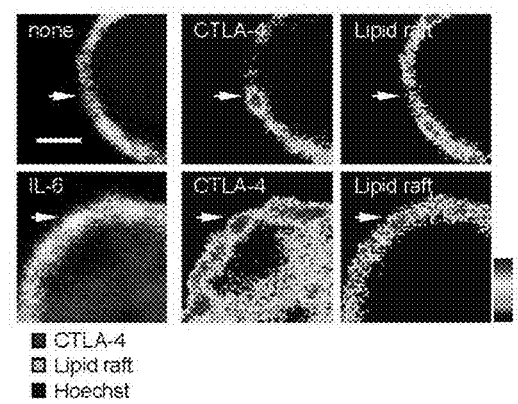
Figure 7A:
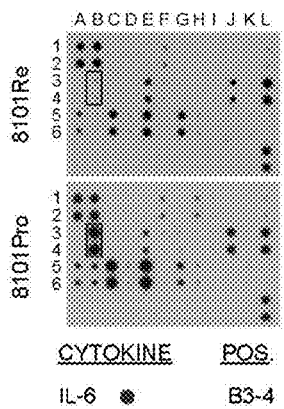
FIGS. 7A-7F: Induced T cell tolerance in IL-6 overexpressing tumors.
Figure 7B:
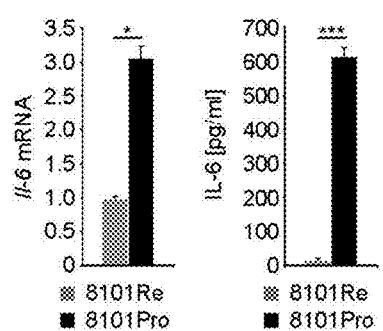
Figure 7C:
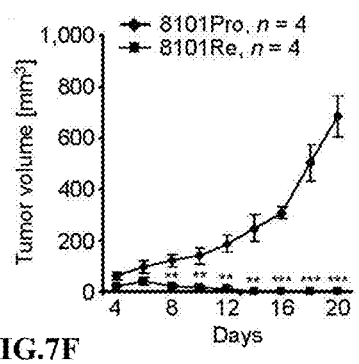
Figure 7D:
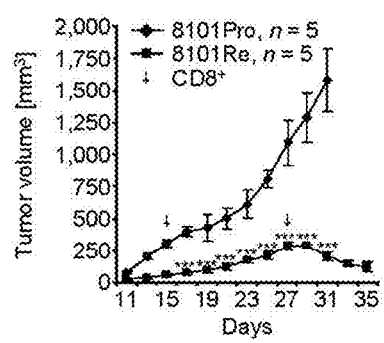
Figure 7E:
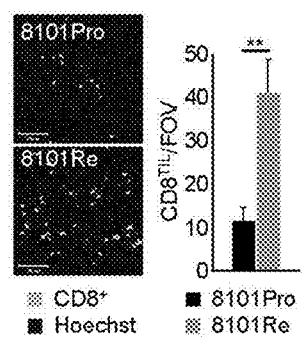
Figure 7F:
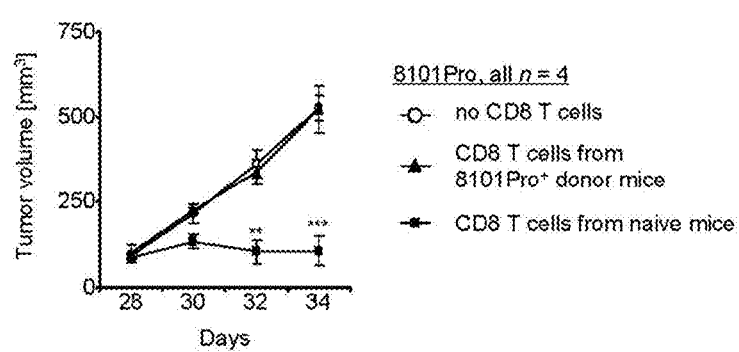

Although CD8$^+$ T cells are known to express low levels of CTLA4, the biological functions of CTLA4 have mainly been characterized in CD4$^+$ T$_{Regs}$ and helper T cells (Wing, K. et al., Science 322:271-275 (2008); Peggs, K. S. et al., J Exp Med 206:1717-1725 (2009); Pandiyan, P. et al., J Exp Med 199:831-842 (2004)). Applicants hypothesized that CTLA4 expression might be upregulated in CD8$^+$ T cells in the tumor milieu. Because IL-6 is highly expressed in many tumors including the progressive fibrosarcoma (FIG. 7A, B), and was capable of inducing T cell tolerance in the tumor-bearing mice (FIG. 7C-F), Applicants tested whether IL-6 could upregulate CTLA4 expression. Western blotting showed an increase in CTLA4 protein expression (FIG. 1G), and confocal microscopy revealed that IL-6 treatment led to an accumulation of CTLA4 protein in lipid raft domains (FIG. 1H), suggesting a functional redistribution of CTLA4 on the surface of CD8$^+$ T cells (Egen, J. G. and Allison, J. P., Immunity 16:23-35 (2002); Baroja, M. L. and Madrenas, J., Am J Transplant 3:919-926 (2003); Chikuma, S. and Bluestone, J. A., Immunol Res 28:241-253 (2003)).

CTLA4$^{apt}$Stat3siRNA Improves CD8$^+$ T Cell Effector Responses In Vivo

Figure 2A:
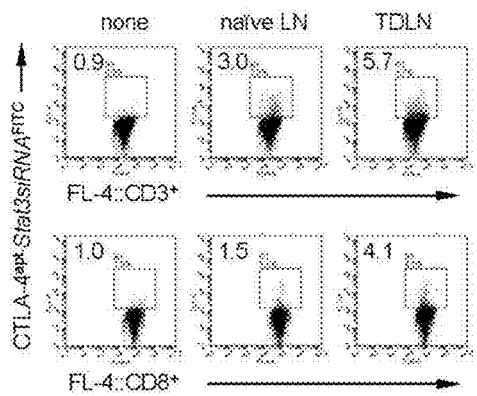
FIGS. 2A-2F: CTLA-4$^{apt}$-Stat3siRNA improves the CD8$^+$ T cell effector response in vivo.
Figure 2B:
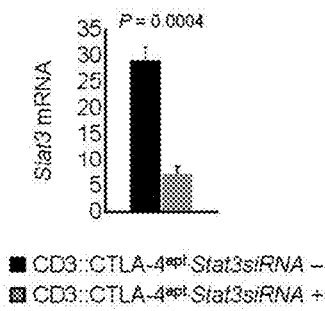
Figure 2C:
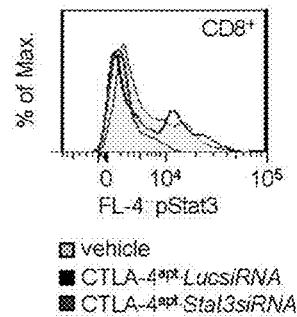
Figure 2D:
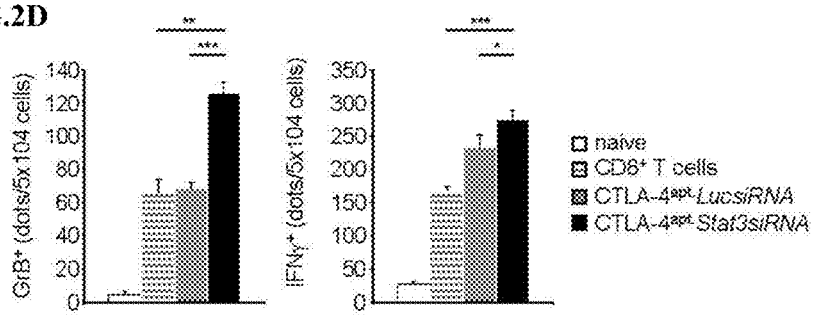
Figure 2E:
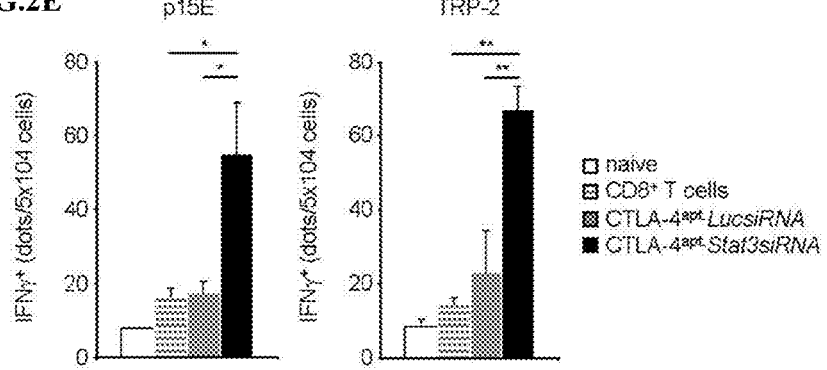
Figure 2F:
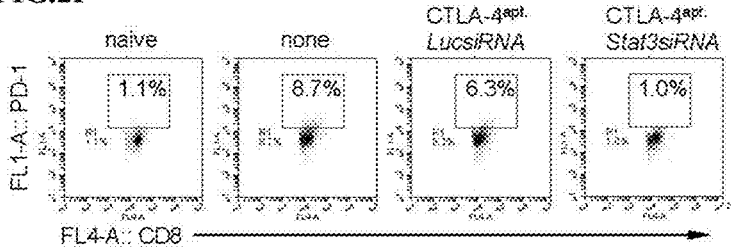

Using mice bearing B16 melanoma tumors, Applicants first confirmed cellular internalization of CTLA4$^{apt}$-Stat3siRNA in vivo by CD3$^+$ T cells and its CD8$^+$ subset isolated from tumor-draining lymph nodes (FIG. 2A, right panels). Notably, CTLA4$^{apt}$-Stat3siRNA uptake by CD8$^+$ T cells was elevated in the tumor draining lymph nodes (TDLNs), compared with LNs from tumor-free mice, consistent with Applicants' hypothesis that tumor milieu/IL-6 upregulated CTLA4 expression, facilitating uptake of the RNA chimera (FIG. 2A, middle panel). Moreover, CTLA4$^{apt}$-Stat3siRNA administration in vivo resulted in efficient Stat3 knockdown in T cells compared to CYLA4$^{apt}$-LucsiRNA or vehicle control treatment (FIG. 2B, C). To assess the antigen-specific CTL activity of tumor-associated CD8$^+$ T cells, Applicants adoptively transferred CD8$^{OT-I}$ cells into Rag1$^{-/-}$ mice bearing B16$^{OVA}$ melanoma tumors. Antigen-specific production of granzyme B and IFN-γ by adoptively transferred CD8$^{OT-I}$ cells was significantly enhanced upon CTLA4$^{apt}$-Stat3siRNA treatment compared with CTLA4$^{apt}$-LucsiRNA, vehicle control, or CD8$^{OT-I}$ alone (FIG. 2D). Moreover, CTLA4$^{apt}$-Stat3siRNA treatment of B16 melanoma enhanced antigen-specific adaptive immune responses to endogenous tumor antigens, p15E and TRP-2, compared with CTLA4$^{apt}$-LucsiRNA, vehicle control, or CD8 T cells alone, as measured by IFN-γ production (FIG. 2E). Furthermore, CYLA4$^{apt}$-Stat3siRNA treatment of B16 tumors reduced PD-1 expression in tumor-associated CD8$^+$ T cells, in contrast to CTLA4$^{apt}$-LucsiRNA or vehicle control treatment (FIG. 2F), suggesting an improved CD8$^+$ T cell effector population and an accumulated CTL response in vivo.

Figure 3A:
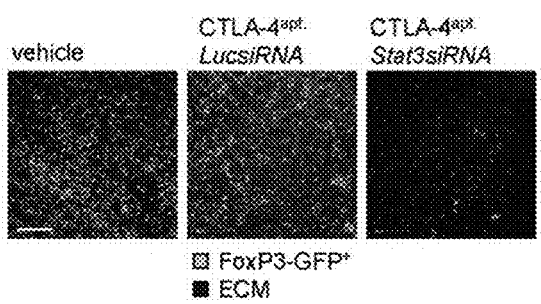
FIGS. 3A-3G: CTLA-4$^{apt}$-Stat3siRNA is effective in inhibiting tumor growth and reducing tumor T$_{Regs}$.
Figure 3C:
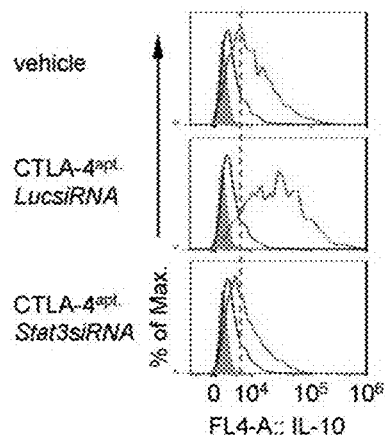
Figure 3B:
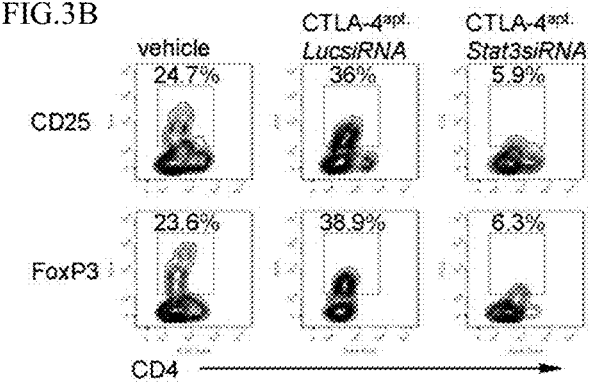
Figure 3D:
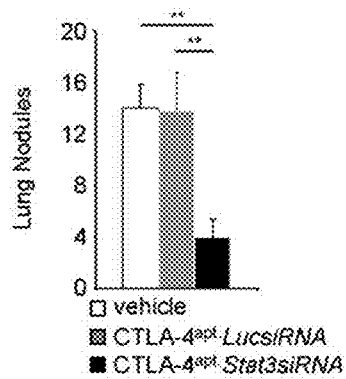
Figure 3E:
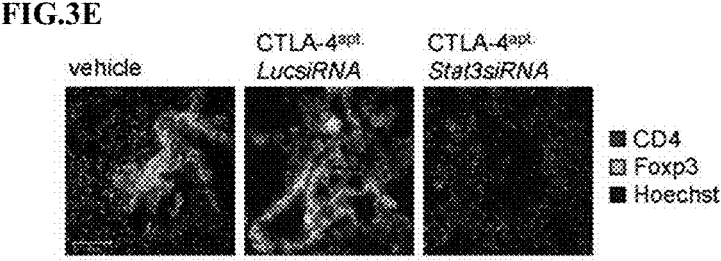
Figure 3F:
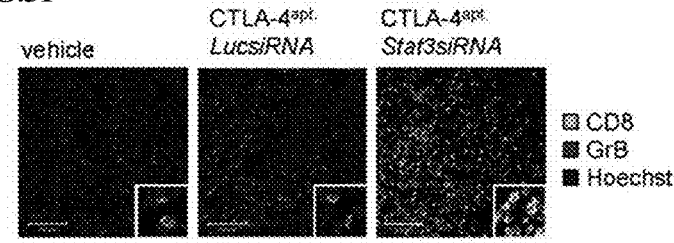
Figure 3F:
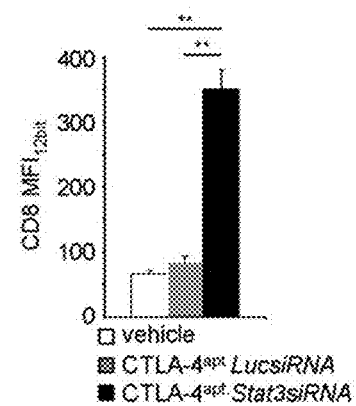

CTLA4$^{apt}$-Stat3siRNA Blocks Tumor T$_{Reg}$ Accumulation and Inhibits Tumor Growth Since tumor-associated FoxP3$^+$ T$_{Regs}$ are a major culprit in tumor-induced immunosuppresion and highly express CTLA4 (Zou), Applicants next tested the effects of CTLA4$^{apt}$-siRNA in targeting this population of T cells. CTLA4$^{apt}$-Stat3siRNA treatment in Foxp3-GFP B16 tumor-bearing mice resulted in a substantial reduction of FoxP3$^+$ T$_{Regs}$, shown by intravital multiphoton microscopy (FIG. 3A). Flow cytometric analysis of CD4$^+$ T cells isolated from tumors of B16 tumor-bearing mice confirmed a reduction in CD4$^+$CD25$^+$FoxP3$^+$ T$_{Regs}$ (FIG. 3B). Moreover, since IL-10 is one of the key mediators in suppression of T cell expansion by T$_{Regs}$ and a downstream target gene of STAT3, Applicants evaluated IL-10 production by tumor-infiltrating T$_{Regs}$. Results from this experiment showed that CTLA4$^{apt}$-Stat3siRNA could effectively reduce tumor-associated T$_{Reg}$ production of IL-10 (FIG. 3C). Applicants further tested whether CTLA4$^{apt}$-Stat3siRNA could be systemically injected to achieve antitumor effects. Mice with B16 melanoma experimental lung metastases were treated systemically with CTLA4$^{apt}$-Stat3siRNA, which led to a significant reduction of lung metastasis (FIG. 3D). Furthermore, a drastic reduction of CD4$^+$Foxp3$^+$ T$_{Regs}$ (FIG. 3E) and an increase in CD8$^+$ T cells in metastatic lungs were observed (FIG. 3F). In addition, CD8$^+$ T cells in the lungs produced more granzyme B, supporting an active antitumor role of CD8$^+$ T cells after systemic treatment of CTLA4$^{apt}$-Stat3siRNA.

Figure 3G:
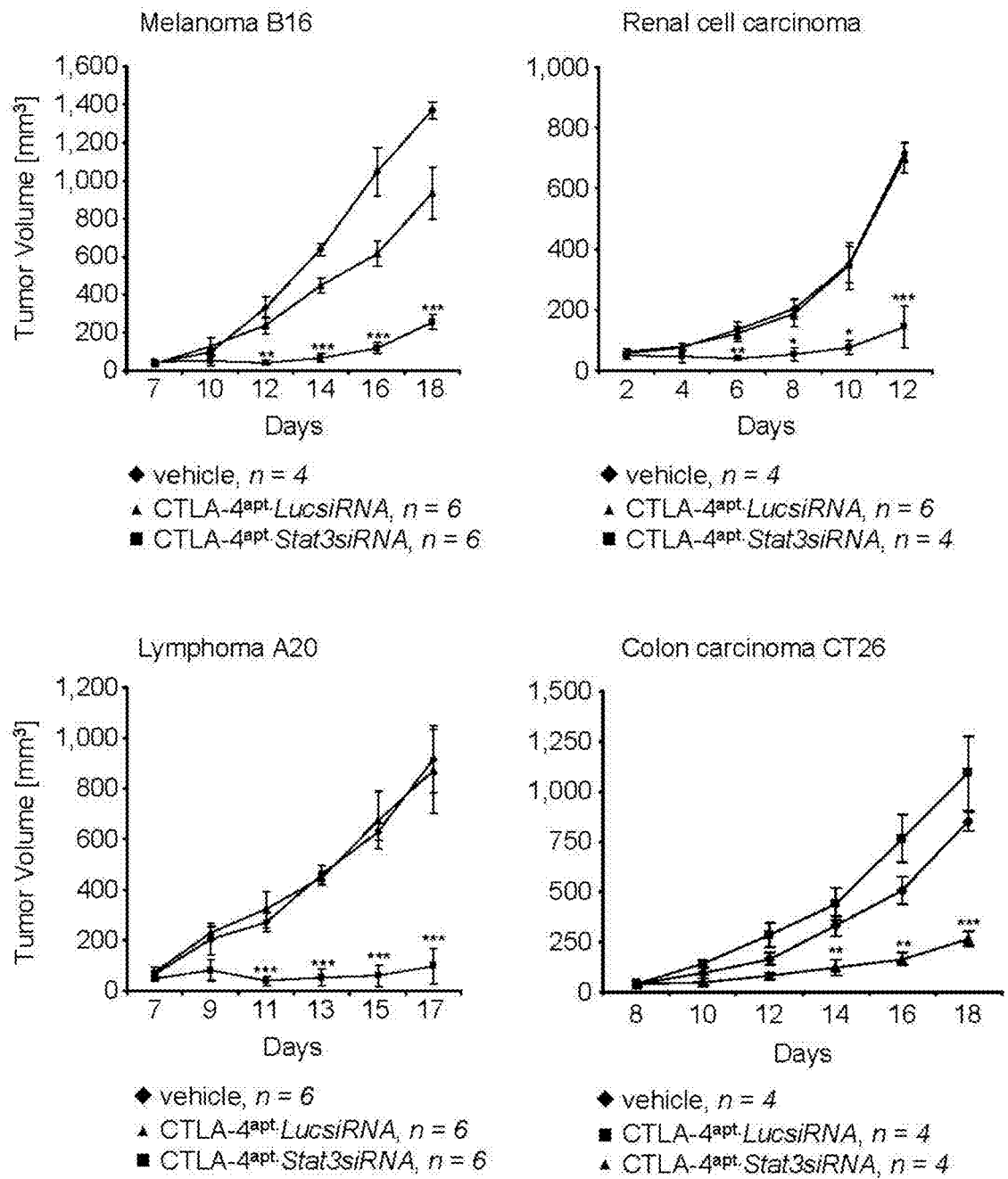

The ability of CTLA4$^{apt}$-Stat3siRNA to silence Stat3 in both CD8$^+$ and CD4$^+$ T cells in the tumor suggested that CTLA4$^{apt}$-Stat3siRNA treatment could induce a potent antitumor effect. In order to evaluate its therapeutic efficacy, Applicants administered CTLA4$^{apt}$-Stat3siRNA, CTLA4$^{apt}$-LucsiRNA, or vehicle control to mice bearing B16 melanoma, Renca renal cell carcinoma, A20 B cell lymphoma, or CT26 colon carcinoma tumors. Results from these experiments showed that CTLA-4$^{apt}$-Stat3siRNA treatments significantly reduced tumor growth in all four murine tumor models (FIG. 3G).

Targeting Human CTLA4 to Deliver siRNA

Figure 4A:
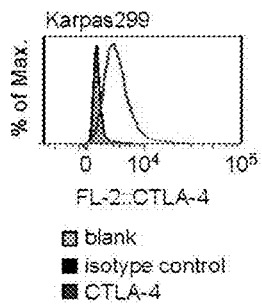
FIGS. 4A-4E: In vivo delivery of CTLA4-aptamer conjugate into CTLA4$^+$ human T cell lymphoma.
Figure 4B:
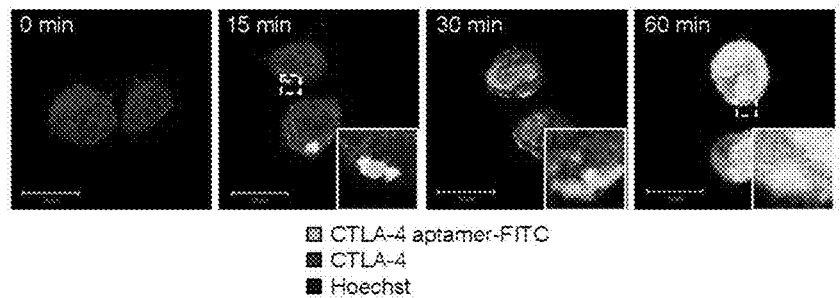
Figure 4C:
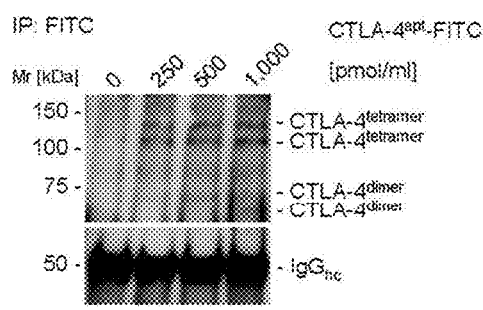
Figure 4D:
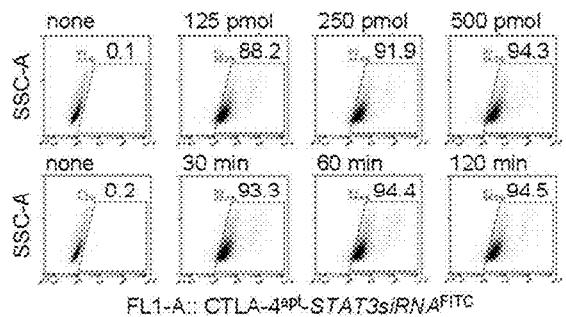
Figure 4E:
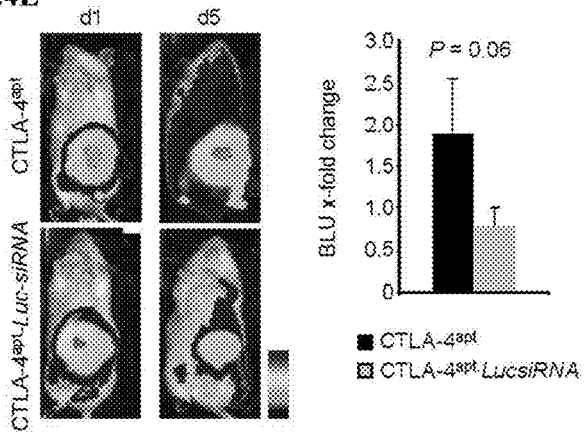
Figures 8A, 8B:
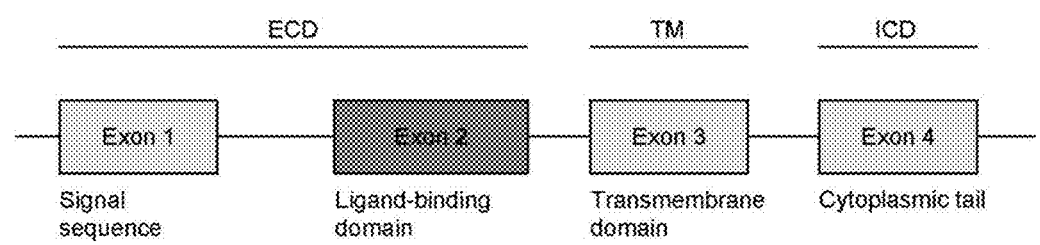
FIGS. 8A-8B: CTLA4 gene and its conservation.
Figure 9:
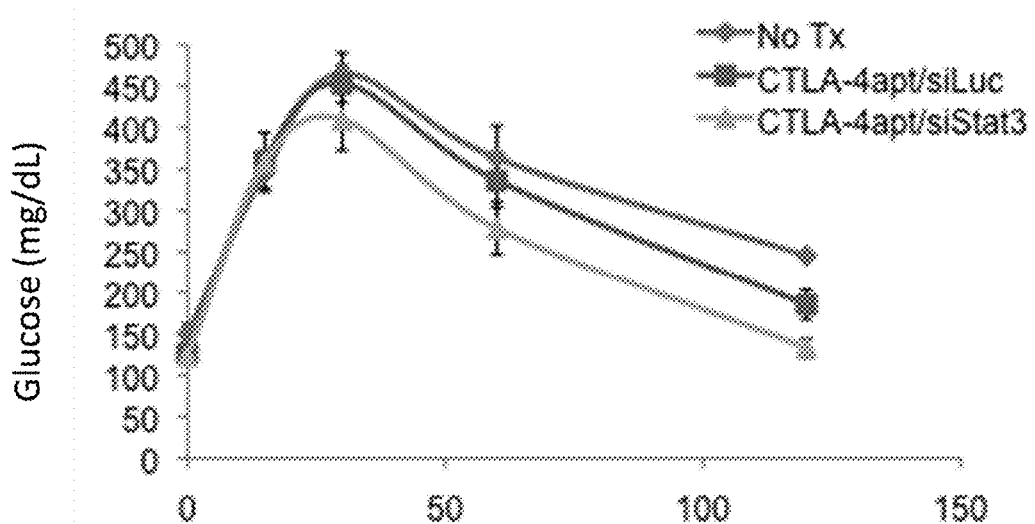
FIG. 9: Blood glucose reduction by treatment with CTLA-4apt-STAT3siRNA. Mice maintained on high-fat diet were treated systemically (via i.v. injection) with CTLA-4apt-STAT3siRNA, CTLA-4apt-LuciferasesiRNA for at least 1 week or left untreated. Improved glucose tolerance was assessed from blood samples for time-points as indicated. Mice were fasted for 16 h, 1 g per kg body weight of glucose injected i.p., and glucose levels were measured every 15-30 min.
Figure 10A:
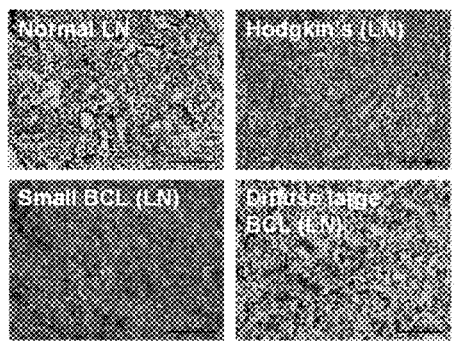
FIGS. 10A-10G: B cell lymphoma treatment with CTLA-4apt-STAT3siRNA.
Figure 10B:
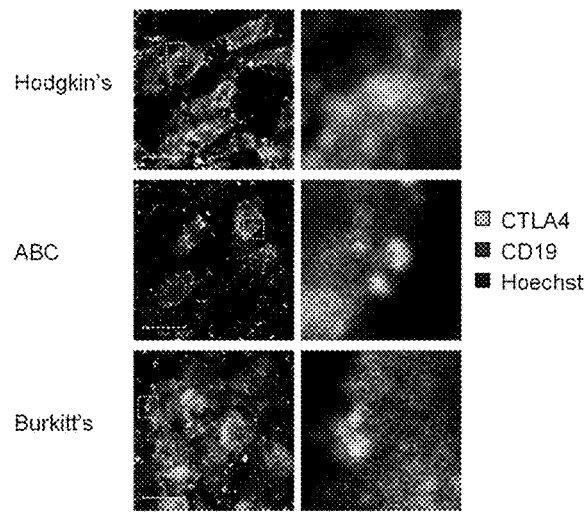
Figure 10C:
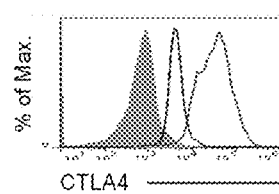
Figure 10D:
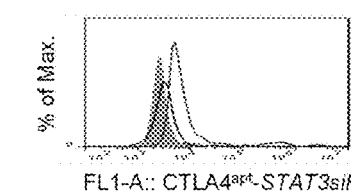
Figure 10E:
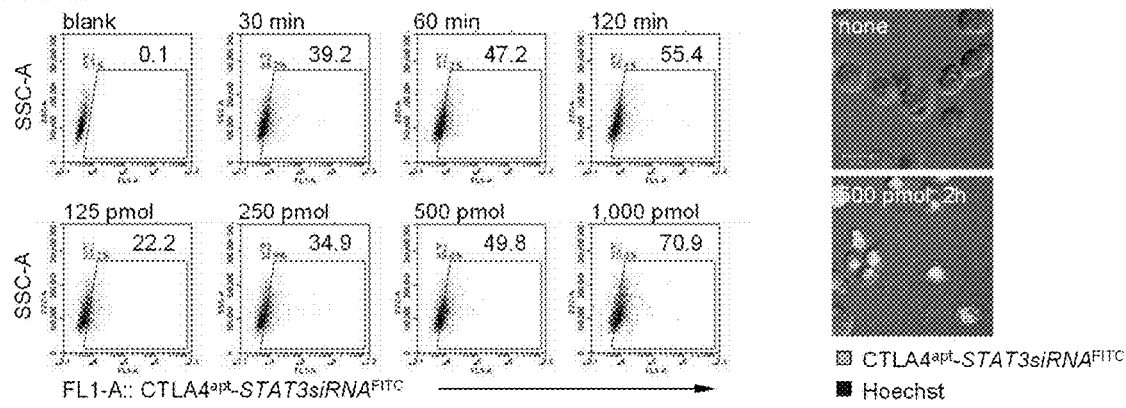
Figure 10F:
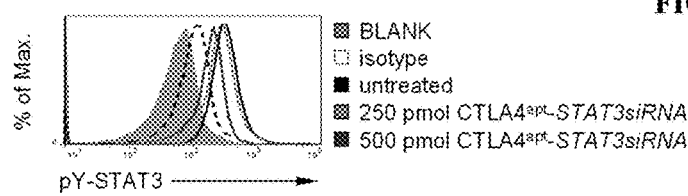
Figure 10G:
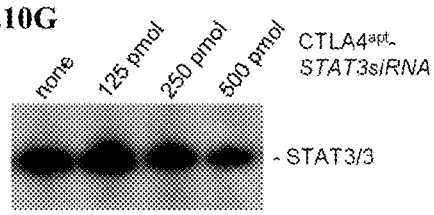
Figure 11H:
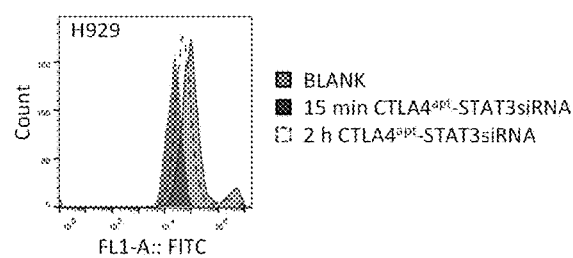
Figure 11I:
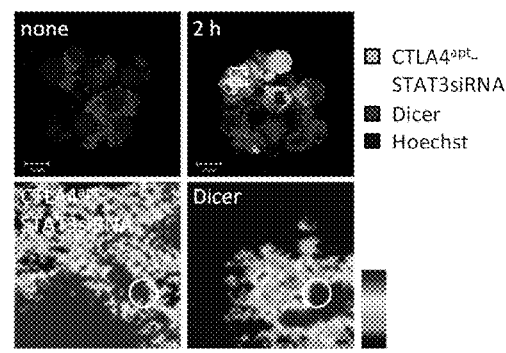
Figure 12A:
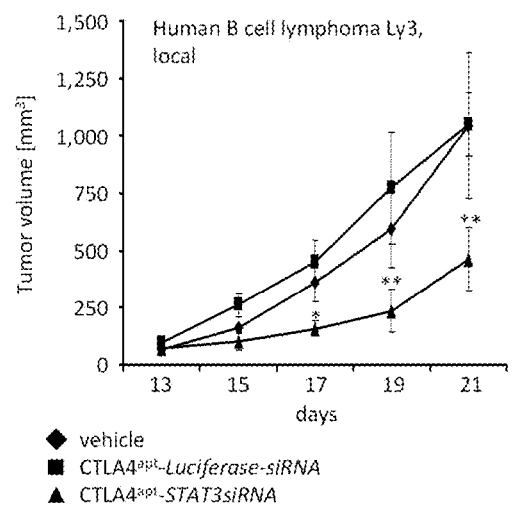
FIGS. 12A-12C: Tumor growth with CTLA4apt-STAT3siRNAFITC treatment.
Figure 12B:
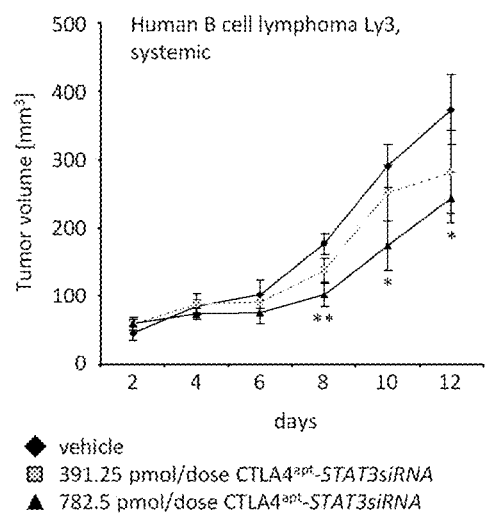
Figure 12C:
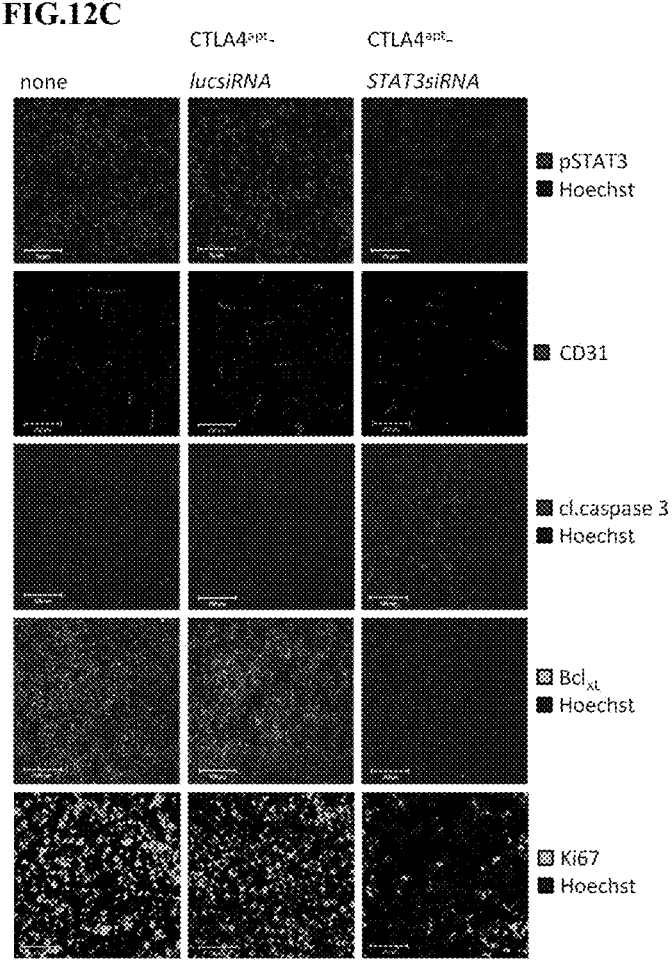
Figure 12C:
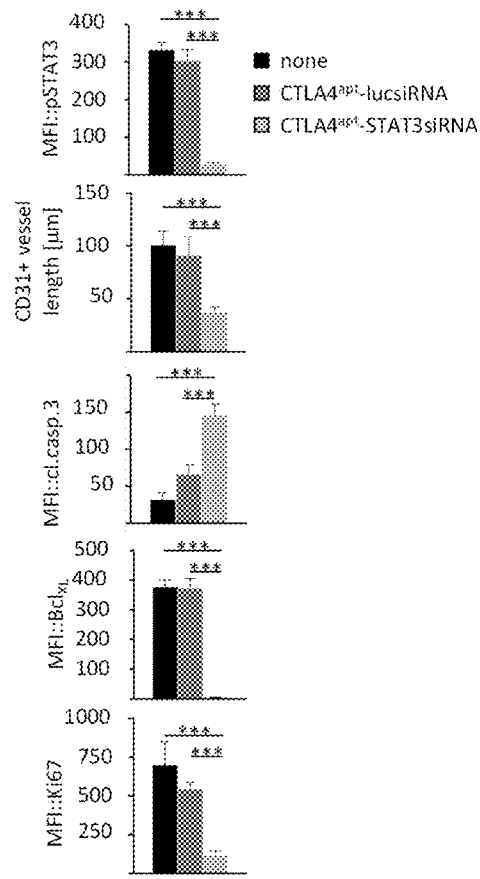

The ligand binding domain of CTLA4 represented by exon 2 coding for amino acids 117-153 harbors the consensus B7 binding motif MYPPPY, which is conserved in mouse and human (FIG. 8). This prompted Applicants to assess CTLA4 aptamer internalization in human CTLA4$^+$ T cell lymphoma cells. Using the CTLA4$^+$ Karpas299 T cell lymphoma (FIG. 4A), Applicants showed that the same CTLA4 aptamers used for siRNA delivery in mouse cells underwent efficient cellular internalization and co-localized with CTLA4 protein in the cytoplasm of the human T cells (FIG. 4B). Furthermore, the CTLA4 aptamer physically interacted with human CTLA4 protein in a dose-dependent fashion (FIG. 4C). Of note, CTLA4 protein complexes of higher order (tetramers and dimers) were co-precipitated, indicating that the CTLA4 aptamer recognizes and binds to functionally assembled CTLA4 complexes. Moreover, malignant human CTLA4$^+$ T cell lymphoma cells readily internalized CTLA4$^{apt}$-siRNA in a dose- and time-dependent fashion as shown by flow cytometry (FIG. 4D). To assess in vivo knockdown efficiency by CTLA4$^{apt}$-siRNA in human T cell lymphomas, Applicants treated Karpas299$^{luc+}$ tumors in a xenograft model with CTLA4$^{apt}$-luciferase-siRNA. Compared to treatment with CTLA4 aptamer alone, the bioluminescent signal was reduced by over 2-fold upon local administration of CTLA4$^{apt}$-luciferase-siRNA (FIG. 4E), indicating a specific and robust in vivo target knockdown.

CTLA4$^{apt}$-STAT3siRNA Inhibits Human Lymphoma Tumor Growth

Figure 5A:
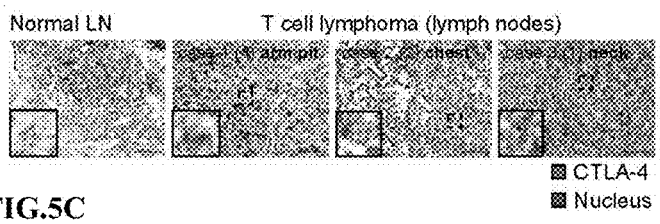
FIGS. 5A-5E: Treating human T cell lymphoma with CTLA4$^{apt}$-STAT3siRNA inhibits tumor growth.
Figure 5B:
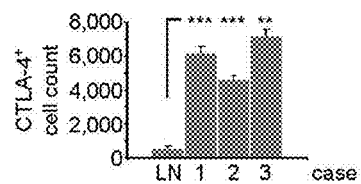
Figure 5C:
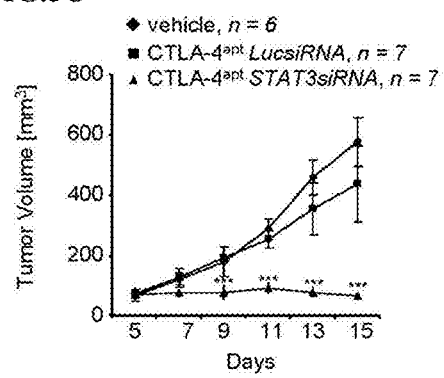
Figure 5D:
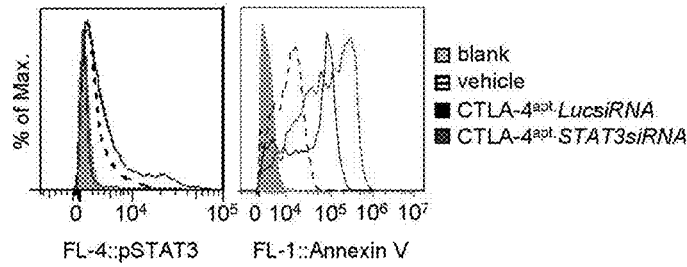
Figure 5E:
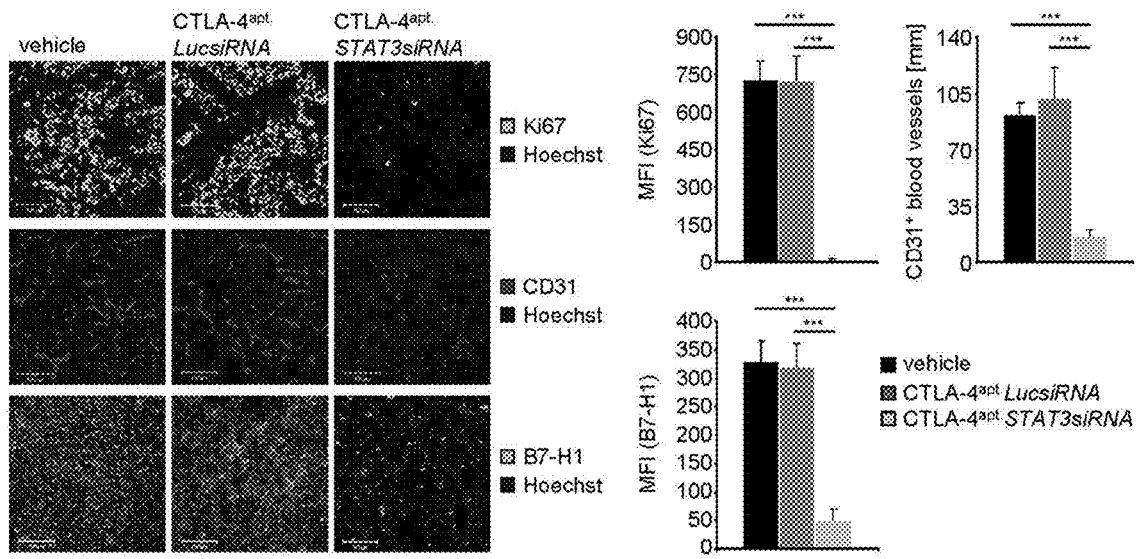

It was previously demonstrated that many types of blood malignancies, including T cell lymphomas, exhibit high CTLA4 expression (Contardi, E. et al., Int J Cancer 117: 538-550 (2005)). Applicants therefore tested the feasibility of blocking STAT3 in T cell lymphoma cells with CTLA4$^{apt}$ linking to a human STAT3siRNA and its potential antitumor effects. Immunohistochemical staining of human T cell lymphoma tissue sections indicated upregulated CTLA4 expression relative to normal lymph nodes (FIG. 5A, B). Treating Karpas299 human T cell lymphoma engrafted in immunodeficient mice resulted in potent tumor growth inhibition (FIG. 5C). Tumor growth inhibition was associated with a drastic decrease in STAT3 activation and induction of tumor cell apoptosis (FIG. 5D). Additionally, Applicants observed decreased proliferation, reduced tumor vasculature, and reduced B7-H1 expression (FIG. 5E).

DISCUSSION

Given the established role of STAT3 in regulating T cell-mediated cancer progression (Kortylewski, M. et al., Nat Med 11:1314-1321 (2005); Herrmann, A. et al., Cancer Res 70:7455-7464 (2010); Kujawski, M. et al., Cancer Res 70:9599-9610 (2010); Brayer, J. et al., Immunol Lett 131: 126-130 (2010)), cell-selective targeted therapeutic strategies to inhibit STAT3 activation in T cells are of tremendous interest for future immunotherapies. In the current study, Applicants describe a novel aptamer-based system to selectively deliver siRNA into tumor-associated T cells expressing CTLA4, including exhausted CD8 T cells and $T_{Regs}$, as well as malignant T cells. CTLA4$^{apt}$-siRNA treatment enables silencing of intracellular checkpoints that are difficult to target with antibodies and small-molecule drugs. CTLA4$^{apt}$-STAT3siRNA treatments improve endogenous adaptive effector functions and induce direct tumor cell killing. While only STAT3 as a therapeutic target in CTLA4-positive cells was tested in the current study, it is anticipated that the CTLA4$^{apt}$-siRNA conjugates are applicable for other checkpoints and immunosuppressive molecules in tumor-associated T cells and in CTLA-4-expressing malignant cells.

Using an antagonistic aptamer recognizing human CD4, Lieberman and colleagues recently demonstrated interrupted HIV transmission and desired RNAi-mediated knockdown of viral genes by the CD4-aptamer-siRNA chimeras (Wheeler, L. A. et al., J Clin Invest 121:2401-2412 (2011)). In these studies, the CD4$^{apt}$-siRNA conjugate targeted all CD4 T cell populations, the primary cellular target of HIV. By contrast, the immunosuppressive tumor microenvironment drives CD8 T cells into exhaustion and promotes $T_{Regs}$, both associated with expression of inhibitory co-receptors, including CTLA-4 and PD-1. Thus, Applicants' studies demonstrate the ability to target specific subsets of T cells— the tumor-associated CD8 T cells and $T_{Regs}$. While its expression is associated with CD8 T cell exhaustion, CTLA4 intracellular signaling has been reported to possess a broad plasticity of cellular responses ranging from inhibition of cytokine production and blunting clonal expansion to T cell survival (Walunas, T. L. et al., Immunity 1:405-413 (1994); Pandiyan, P. et al., J Exp Med 199:831-842 (2004); Linsley, P. S. et al., J Exp Med 176:1595-1604 (1992); Linsley, P. S. et al., Science 257:792-795 (1992); Madrenas, J. et al., J Immunol 172:5948-5956 (2004)). In Applicants' prior investigations, Applicants validated that STAT3 critically contributes to the inhibition of adaptive antitumor immune responses (Kortylewski, M. et al., Nat Med 11:1314-1321 (2005); Kujawski, M. et al., Cancer Res 70:9599-9610 (2010)). These observations provided a previously unexplored opportunity to selectively target tumor-associated exhausted CD8 T cell populations to restore effector functions and augment an antigen-specific CTL population by directed STAT3 gene silencing.

CTLA4$^{apt}$-siRNA conjugates preferentially undergo cellular internalization in CD4, and CD8 T cells. However, the conjugates are also found in macrophages and dendritic cells to a lesser extent, which potentially could support the adaptive antitumor immune response through STAT3 knockdown in antigen-presenting cells. The uptake by antigen presenting cells of aptamer-siRNA was also observed in the study using the CD4 aptamer-siRNA, which seemed to contribute to the efficacy of the chimera in vivo (Wheeler). Furthermore, CTLA4$^{apt}$-STAT3siRNA treatments, administered locally or systemically, tremendously reduce CD4$^+$ CD25$^+$FoxP3$^+$ $T_{Reg}$ populations in primary tumors as well as in melanoma lung metastases, indicating modulation of the tumor immunologic environment in favor of an increased antitumor capability by CD8 T cells. In mouse tumor models, CTLA4$^{apt}$-STAT3siRNA administration shows a robust inhibition of tumor growth and metastasis. However, CTLA4-aptamer alone, reported to efficiently block CTLA4, did not improve CTL effector function or impact $T_{Reg}$ populations in the tumor. This is likely due to the fact that CTLA4 aptamer used by Gilboa and colleagues (Santulli-Marotto, S. et al., Cancer Res 63:7483-7489 (2003)) was assembled into tetrameric forms of higher antagonistic activity, while STAT3siRNA was synthetically fused to a monomeric CTLA4 aptamer. However, due to the lethal hyperimmune phenotype of Ctla-4 knockout mice (Tivol, E. A. et al., Immunity 3:541-547 (1995); Waterhouse, P. et al., Science 270:985-988 (1995)) and certain adverse events in patients treated with CTLA-4 blocking antibodies (Wing, K. et al., Science 322:271-275 (2008); Leach, D. R. et al., Science 271:1734-1736 (1996)), an aptamer with additional potent effects antagonizing CTLA4 in the siRNA conjugate may not be necessary.

Besides tumor-associated T cell populations, malignant T cell lymphoma and other blood malignancies, also express CTLA4 (Wong, H. K. et al., J Invest Dermatol 126:212-219 (2006); Xerri, L. et al., J Pathol 183:182-187 (1997); Kosmaczewska, A. et al., Leukemia 19:301-304 (2005)). Many of these blood malignancies also display elevated STAT3 activation (Scuto, A. et al., Cancer Res 71:3182-3188 (2011); Holtick, U. et al., Leukemia 19:936-944 (2005); Sommer, V. H. et al., Leukemia 18:1288-1295 (2004); Liu, Y. et al., Blood 120:1458-1465 (2012)). In non-malignant T cells, CTLA4 oligomerization on the cell surface readily accumulating in the immunological synapse is considered to depend on ligand activation, and therefore represents a biologically active form of CTLA4 (Egen, J. G. and Allison, J. P., Immunity 16:23-35 (2002); Egen, J. G. et al., Nat Immunol 3:611-618 (2002); Darlington, P. J. et al., J Immunol 175:996-1004 (2005)). CTLA4 has also been reported to exist at least dimerized prior to ligation (Darlington, P. J. et al., J Immunol 175:996-1004 (2005); Linsley, P. S. et al., J Biol Chem 270:15417-15424 (1995)), indicating the possibility that CTLA4 oligomerizes in a ligand-independent manner in human T cell lymphoma. However, Applicants' results indicate that CTLA4$^{apt}$-STAT3siRNA efficiently inhibits T cell lymphoma growth concomitant with considerably reduced STAT3 activation. Compared to antagonistic antibodies targeting immune checkpoints, the CTLA4$^{apt}$-siRNA chimera additionally directly reduces tumor cell growth and their immunosuppressive impact on the T cells in the tumor microenvironment.

Methods

Mice and cell culture. Mouse care and experimental procedures with mice were performed under pathogen-free conditions in accordance with established institutional guidance and approved protocols from the Research Animal Care Committees of the City of Hope. For subcutaneous tumor challenge, C57BL/6, Rag1(ko)Momj/B6.129S7, Foxp3-

GFP(ki)/B6, Balb/c (The Jackson Laboratory), were injected with $10^5$ B16 melanoma or ovalbumin expressing B16$^{OVA}$, 2.5×$10^5$ A20 lymphoma, colon carcinoma CT26, or renal clear cell carcininoma (Renca), or 10×$10^6$ 8101 fibrosarcoma regressor or progressor, respectively. For antigen specific analyses, transgenic Ova TCR (OT-I) mice were obtained from The Jackson Laboratory. Athymic nu/nu mice (NCI Frederick) were engrafted with $10^6$ Karpas299 or Karpas299$^{luc+}$ human lymphoma cells s.c. into the flank. After tumors reached 5-7 mm in diameter, treatment with 782.5 pmol/dose/mouse CTLA4-aptamer was administered every other day. For experimental induction of metastases by lung colonization, 5×$10^4$ B16 melanoma cells were injected i.v. via retro-orbital route. Mice which received systemic tumor cell engraftment were treated every other day with 782.5 pmol/dose/mouse CTLA4-aptamer administered intravenously.

Fibrosarcoma 8101 subclones (kind gift of Dr. Hans Schreiber, University of Chicago, Ill.) were cultured in DMEM medium (Gibco) supplemented with 10% FBS (Sigma). Mouse melanoma B16 (kindly provided by Dr. Drew Pardoll, Johns Hopkins, Baltimore, Md.) and B16$^{OVA}$ (provided by Dr. J. Mule, Moffitt Cancer Center, Tampa, Fla.), colorectal adenocarcinoma CT26 (ATCC), renal carcinoma Renca (provided by Dr. Alfred Chang, University of Michigan Medical Center, Ann Arbor, Mich.), A20 B cell lymphoma (ATCC), and human Karpas299 T cell lymphoma (ATCC) were grown in RPMI1640 (Gibco) containing 10% FBS.

Adoptive T-cell transfer and ELISpot Assay. B16 or B16$^{OVA}$ cells were injected s.c. into Rag1$^{-/-}$ mice and CD8 or CD8$^{OT-I}$ T cells (8×$10^6$ to 10×$10^6$) were adoptively transferred via retro-orbital route when tumors reached an average diameter of 5 mm. T cells were isolated from spleens and lymph nodes of donor mice using negative selection (EasySep, StemCell Technologies). For antigen-specific responses of CD8 T cells, 5×$10^5$ lymphocytes isolated from tumor-draining lymph nodes as well as from lymph nodes of naïve mice were seeded into a 96-well filtration plate and the CD8 T cell effector response was recalled using 10 μg/mL peptide (TRP2$^{SVYDFFVWL}$, OVA$^{SIINFEKL}$ were obtained from AnaSpec; p15E$^{KSPWFTTL}$ was generated by the DNA/RNA and Protein Synthesis Core Facility at the City of Hope) for 24 hours at 37° C. Peptide-specific granzyme B and IFN-γ-positive spots were detected according to the manufacturer's instructions (R&D Systems, Diaclone).

Imaging. Indirect immunoflourescence has been carried out as described previously (Herrmann, A. et al., *Cancer Res* 70:7455-7464 (2010)) staining EEA1, CTLA-4, B7-H1 (Santa Cruz), Hoechst33342 (Sigma), lipid rafts (cholera toxin subunit B, Invitrogen), CD4, CD31 (BD Biosciences), Foxp3, granzyme B, Ki67 (abeam). Non-invasive bioluminescent imaging was performed according to the manufacturer's instructions using Ivis 100 (Xenogen). D-Luciferin substrate was obtained from Caliper. In vivo multiphoton microscopy (IVMPM) of melanoma B16 tumors engrafted in C57BL/6 mice expressing GFP under control of the Foxp3 promoter, was performed while mice were anaesthetized with isoflurane/oxygen. For IVMPM, an Ultima Multiphoton Microscopy System was used (Prairie Technologies). For imaging GFP, the excitation wavelength was set to λ=890 nm. Band-pass filters optimized for GFP (BP λ=525/50 nm) was used for detection. Signals of the extracellular matrix are given by second harmonic generation at excitation wavelength λ=890 nm and was detected with BP λ=460/50 nm.

Flow cytometry. Cell suspensions and tumor tissues were prepared as described previously (Herrmann, A. et al., *Cancer Res* 70:7455-7464 (2010)) and stained with different combinations of fluorophore-coupled antibodies to CD3, CD4, CD8, CD11b, CD11c, CD19, CD25, CD45, F4/80, CTLA4, phospho-Tyr705-Stat3, IL-10 (BD Biosciences). Annexin V-FITC was purchased from BioVision. Fluorescence data were collected on Accuri (BD Accuri C6) and analyzed using FlowJo software (Tree Star).

Immunoblotting, immunoprecipitation, Cytokine Array, and ELISA. Whole cell lysates were prepared using RIPA lysis buffer containing 50 mM Tris (pH 7.4), 150 mM NaCl, 1 mM EDTA, 0.5% NP-40, 1 mM NaF, 15% glycerol, and 20 mM β-glycerolphosphate. A protease inhibitor cocktail was added fresh to the lysis buffer (Mini Protease Inhibitor Cocktail, Roche). Normalized protein amounts were subjected to electrophoretic separation by SDS-PAGE, transferred onto nitrocellulose for western blotting, and subsequently immunodetection was performed using antibodies against CTLA4, STAT3 (Santa Cruz), and β-actin (Sigma). For co-immunoprecipitation, anti-FITC antibody (Invitrogen) was used to label rProtein G agarose beads (Invitrogen), which were subsequently incubated for 16 h with whole cell lysates, subjected to electrophoretic protein separation and western blot detection. For determination of cytokine expression profiles, supernatants of fibrosarcoma 8101Re and 8101Pro were collected from a 24 h cell culture. Tumor cell supernatants were subjected to cytokine arrays and analyzed according to the manufacturer's instructions (RayBiotech). IL-6 cytokine production by fibrosarcoma 8101Re and 8101Pro was determined from a 24 h cell culture as described above and analyzed according to the manufacturer's instructions (eBioscience).

Polymerase Chain Reaction. Transcript amplification was determined from total RNA purified using RNeasy Kit (QIAGEN). cDNA was synthesized using the iScript cDNA Synthesis Kit (Bio-Rad). Real-time PCR was performed in triplicates using the Chromo4 Real-Time Detector (Bio-Rad). The murine Gapdh housekeeping gene was used as an internal control to normalize target gene mRNA levels. Primers were obtained from SA Biosciences (mouse Stat3: PPM04643E-200, mouse Il-6: PPM03015A-200).

What is claimed is:

1. A method of stimulating the immune system of a subject in need thereof, said method comprising administering to a subject a therapeutically effective amount of a CTLA-4 aptamer nucleic acid conjugated to a cell activity modulating nucleic acid, wherein said cell activity modulating nucleic acid is a FoxP3 antisense nucleic acid, an anti-tyrosine kinase antisense nucleic acid, or a Signal Transducer and Activator of Transcription (STAT) antisense nucleic acid, thereby stimulating the immune system of said subject.

2. The method of claim 1, wherein stimulating the immune system comprises maturation, differentiation, or proliferation of natural killer cells, T cells, monocytes, or macrophages.

3. The method of claim 1, wherein stimulating the immune system comprises an increase in a $T_H1$-type immune response.

4. The method of claim 1, wherein stimulating the immune system comprises stimulating a plasmacytoid dendritic cell, myeloid dendritic cell, myeloid-derived suppressor cell, macrophage, B cell, activated NK cell, or activated neutrophil.

5. The method of claim 1, wherein stimulating the immune system comprises increasing the activity of a cytotoxic T cell.

6. The method of claim 5, wherein the cytotoxic T cell is a tumor-specific cytotoxic T cell.

7. The method of claim 1, wherein said CTLA-4 aptamer nucleic acid is conjugated to said cell activity modulating nucleic acid through a linker.

8. The method of claim 7, wherein said linker comprises a non-nucleic acid spacer.

9. The method of claim 8, wherein said non-nucleic acid spacer connects said cell activity modulating nucleic acid to the 3' terminal end of said linker nucleic acid sequence.

10. The method of claim 7, wherein said linker connects said cell activity modulating nucleic acid to the 3' terminal end of said CTLA-4 aptamer nucleic acid.

11. The method of claim 1, wherein said antisense nucleic acid is a siRNA.

12. The method of claim 1, wherein said cell activity modulating nucleic acid is a FoxP3 antisense nucleic acid.

13. The method of claim 1, wherein said cell activity modulating nucleic acid is an anti-tyrosine kinase antisense nucleic acid.

14. The method of claim 1, wherein said cell activity modulating nucleic acid is a Signal Transducer and Activator of Transcription (STAT) antisense nucleic acid.

* * * * *

UNITED STATES PATENT AND TRADEMARK OFFICE
CERTIFICATE OF CORRECTION

PATENT NO. : 11,186,840 B2
APPLICATION NO. : 16/892995
DATED : November 30, 2021
INVENTOR(S) : Hua Yu et al.

Page 1 of 1

It is certified that error appears in the above-identified patent and that said Letters Patent is hereby corrected as shown below:

On the Title Page

Item (72) replace with the following:
"(72) Inventors: Hua Yu, Glendora, CA (US); Andreas Herrmann, Pasadena, CA (US); Marcin Tomasz Kortylewski, Monrovia, CA (US); Piotr Marek Swiderski, San Dimas, CA (US)"

Signed and Sealed this
Fifteenth Day of August, 2023

Katherine Kelly Vidal
*Director of the United States Patent and Trademark Office*